US012746318B2

(12) United States Patent
Kwon et al.

(10) Patent No.: US 12,746,318 B2
(45) Date of Patent: Sep. 29, 2026

(54) BLOOD PERFUSION DEVICE TO REDUCE SECONDARY INFECTION IN HOSPITAL

(71) Applicant: SEOUL NATIONAL UNIVERSITY R&DB FOUNDATION, Seoul (KR)

(72) Inventors: Woon Yong Kwon, Seoul (KR); Gil Joon Suh, Seoul (KR); Jung Chan Lee, Seoul (KR); Sung Hee Kim, Seoul (KR); Areum Lee, Seoul (KR); Jeong Yeon Kim, Seoul (KR); Yoon Sun Jung, Seoul (KR); Kyung Su Kim, Seoul (KR); Taegyun Kim, Seoul (KR); Ha Young Kim, Seoul (KR); Heesu Park, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 354 days.

(21) Appl. No.: 18/568,134

(22) PCT Filed: Nov. 29, 2023

(86) PCT No.: PCT/KR2023/019443
§ 371 (c)(1),
(2) Date: Dec. 7, 2023

(87) PCT Pub. No.: WO2024/128630
PCT Pub. Date: Jun. 20, 2024

(65) Prior Publication Data
US 2025/0114511 A1 Apr. 10, 2025

(30) Foreign Application Priority Data
Dec. 16, 2022 (KR) ........................ 10-2022-0176528

(51) Int. Cl.
*A61M 1/36* (2006.01)

(52) U.S. Cl.
CPC ....... *A61M 1/3687* (2013.01); *A61M 2202/20* (2013.01)

(58) Field of Classification Search
CPC ........ A61M 1/34; A61M 1/36; A61M 1/3687; A61M 2202/20; A61M 2202/0447; A61M 1/3679; A61M 1/3673; A61M 2202/0057
See application file for complete search history.

(56) References Cited

U.S. PATENT DOCUMENTS

2016/0082177 A1* 3/2016 Ward .................. A61M 1/3679 210/691

FOREIGN PATENT DOCUMENTS

JP 2008-503273 A 2/2008
JP 2022-550403 A 12/2022
(Continued)

OTHER PUBLICATIONS

Kwon et al., Circulating mitochondrial N-formyl peptides contribute to secondary nosocomial infection in patients with septic shock, Apr. 22, 2021, PNAS, 118(17), 1-11 (Year: 2021).*
(Continued)

*Primary Examiner* — Susan S Su
*Assistant Examiner* — Erin A Kim
(74) *Attorney, Agent, or Firm* — SALIWANCHIK, LLOYD & EISENSCHENK

(57) ABSTRACT

The present disclosure relates to a blood perfusion device, and more specifically to a blood perfusion device which includes an anti-mtFP antibody to remove mtFP, thereby blocking the binding of mtFP to formyl peptide receptor 1 (FPR1) on the PMN membrane by removing the mtFP, and is capable of suppressing the occurrence of secondary infection in hospital by restoring the chemotaxis of polymorphonuclear leukocytes (PMN).
The present disclosure can reduce late death and improve long-term survival by improving the clinical course of sepsis
(Continued)

patients recovering after the acute phase, and it is expected to improve long-term survival by suppressing the occurrence of secondary infections in hospital for patients who require long-term hospitalization in the intensive care unit or hospital room, such as severe trauma patients, organ transplant patients and patients surviving after cardiac arrest.

8 Claims, 20 Drawing Sheets

(56) References Cited

FOREIGN PATENT DOCUMENTS

| | | | |
|---|---|---|---|
| KR | 10-2017-0020749 | A | 2/2017 |
| KR | 10-2017-0060062 | A | 5/2017 |

OTHER PUBLICATIONS

International Search Report dated Mar. 19, 2024 in International Application No. PCT/KR2023/019443.

Kwon, W.Y., et al., "Circulating mitochondrial N-formyl peptides contribute to secondary nosocomial infection in patients with septic shock," PNAS, Apr. 22, 2021, 118(17):1-12.

* cited by examiner

BLOOD PERFUSION DEVICE TO REDUCE SECONDARY INFECTION IN HOSPITAL

CROSS-REFERENCE TO RELATED APPLICATIONS

This application is the U.S. national stage application of International Patent Application No. PCT/KR2023/019443, filed Nov. 29, 2023, which claims the benefit under 35 U.S.C. § 119 of Korean Application No. 10-2022-0176528, filed Dec. 16, 2022, the disclosures of each of which are incorporated herein by reference in their entirety.

BACKGROUND

1. Field of the Invention

The present disclosure relates to a blood perfusion device, and more specifically to a blood perfusion device which includes an anti-mitochondrial N-formyl peptide (mtFP) antibody to remove mtFP, thereby blocking the binding of mtFP to formyl peptide receptor 1 (FPR1) on the PMN membrane by removing the mtFP, and is capable of suppressing the occurrence of secondary infection in hospital by restoring the chemotaxis of polymorphonuclear leukocytes (PMN).

2. Discussion of Related Art

Immune paralysis increases susceptibility to secondary infections and worsens the clinical outcome of septic shock patients who survive the initial hyperinflammatory phase. The chemotaxis of polymorphonuclear leukocytes (PMN) to sites of secondary infection is important in inhibiting progression to secondary invasive infection in patients with septic shock. During septic shock, multiorgan damage occurs primarily due to systemic inflammation, and secondarily, tissue hypoperfusion causes mitochondrial N-formyl peptide (mtFP) to be released into the circulation system. Circulating mtFP binds to formyl peptide receptorl (FPR1) on PMN membranes. This binding internalizes FPR1 (homologous internalization) and other chemokine receptors (heterologous internalization) into the cytoplasm and blocks FPR1 from binding to newly synthesized bacterial peptides. Additionally, it blocks the binding of newly released chemokines to other chemokine receptors and secondarily inhibits PMN chemotaxis to the site of infection. It is known that after internalization of the FPR1-mtFP complex, mtFP is removed from the endosomal compartment, and FPR1 is rapidly recycled to the PMN membrane or degraded by lysosomes.

The inventors of the present disclosure have confirmed in previous studies that increased circulating mtFP levels are independently associated with the development of secondary infections and 90-day mortality in patients recovering from septic shock, and increased susceptibility to secondary infection is mainly due to the inhibition of FPR1-mediated PMN chemotaxis, and it was confirmed that circulating mtFP does not affect the bactericidal activity of PMN.

Furthermore, the inventors of the present disclosure confirmed that blocking FPR1 can preserve other chemokine receptors on PMN membranes by inhibiting heterologous internalization of non-FPR1 chemokine receptors. However, in septic shock patients, FPR1 blocking may not be an effective treatment to rescue PMN chemotaxis to secondary infection sites. In a previous study, in order to reduce secondary infections in hospitals that occur after the end of acute treatment for severe trauma patients, there were efforts to maintain the migration of neutrophils (PMN) to the site of secondary bacterial infection by inhibiting the intracellular movement of other chemotactic receptors instead of giving up the activity of FPR1 by administering an antagonist that blocks the mtFP binding site of FPR1. However, in sepsis patients, the concentration of chemokine in the systemic blood is relatively high, and the difference between the concentration of chemokine at the site of secondary bacterial infection and the concentration of systemic chemokine is not large, thereby reducing the effectiveness of using FPR1 antagonists. Actually, in a previous study, plasma chemokine levels were significantly higher at admission in patients with septic shock, as well as at the onset of secondary infection in patients recovering from septic shock, than in healthy volunteers. Unlike trauma patients, in patients recovering from septic shock, the chemokine gradient from the circulation system to the site of secondary infection may not be sufficient to induce PMN chemotaxis. In this situation, formyl peptide receptor 1 (FPR1)-mediated chemotaxis against newly synthesized bacterial peptides will be responsible for a significant portion of PMN migration to the sites of secondary infection.

Accordingly, the inventors of the present disclosure made diligent efforts to develop a technique to rescue PMN chemotaxis and inhibit the development of secondary infection in patients recovering from septic shock, and as a result, since FPR1, which can bind to newly synthesized bacterial peptides, must be preserved as much as possible in the PMN membrane, mtFP itself is removed from the blood through an antibody, thereby blocking the rebinding of mtFP to FPR1 re-expressed on the surface of neutrophils, and the FPR1-mediated chemotaxis of neutrophils to the sites of secondary bacterial infection is restored, thereby completing the present disclosure.

SUMMARY OF THE INVENTION

An object of the present disclosure is to provide a blood perfusion device for reducing secondary infection in hospital.

In order to achieve the above object, in one aspect, the present disclosure provides a blood perfusion device, including a blood inlet for allowing blood to flow into the device; an adsorption medium including an anti-mitochondrial N-formyl peptides antibody (anti-mtFP antibody); and a blood outlet for allowing blood to flow out of the device.

In the present disclosure, the blood perfusion device may suppress the occurrence of secondary infection in hospital.

In the present disclosure, a target subject of the blood perfusion device may be at least one selected from the group consisting of sepsis patients, septic shock patients, severe trauma patients, organ transplant patients, hemorrhagic shock patients, myocardial infarction patients, cardiogenic shock patients, stroke patients and patients surviving after cardiac arrest.

In the present disclosure, the mtFP may be at least one selected from the group consisting of mitochondrial NADH-ubiquinone oxidoreductase chain 6 (MT-ND6), MT-ND3, MT-ND4, MT-ND5 and mitochondrial cytochrome c oxidase 1 (MT-COX1).

In the present disclosure, the blood perfusion device may further include oxygen, a blood-anticoagulant and leukotriene B4 (LTB4), and the leukotriene B4 (LTB4) may be included at a concentration of 10 to 100 μg/mL.

In the present disclosure, the adsorption medium may include the anti-mtFP antibody at a concentration of 0.5 μg/mL to 20.0 μg/mL.

In the present disclosure, the adsorption medium may have an anti-mtFP antibody attached or coated on a surface thereof.

In the present disclosure, the adsorption medium may be at least one selected from the group consisting of fiber form, bead form, film form and hollow-fiber form.

The present disclosure can suppress the progression of systemic secondary infection through the sterilizing effect of neutrophils on secondary infected bacteria by restoring the chemotaxis of neutrophils (PMN) to the site of secondary infection, and this can reduce late-term mortality and improve long-term survival by improving the clinical course of sepsis patients who are recovering after the acute phase.

In addition, the present disclosure has the advantage of being applicable to all cases where secondary infections may occur in the hospital after the completion of acute treatment in diseases that have pathophysiology that allows mtFPs to be released from damaged tissues into the blood. In particular, it is expected to improve long-term survival by suppressing the occurrence of secondary infections in hospitals for patients who require long-term hospitalization in the intensive care unit or hospital room, such as severe trauma patients, organ transplant patients and patients surviving after cardiac arrest.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 1 shows that in sepsis patients, when mitochondrial NADH-ubiquinone oxidoreductase chain 6 (MT-ND6), MT-ND3, MT-ND4, MT-ND5 and mitochondrial cytochrome c oxidase 1 (MT-COX1) are selectively removed by using specific antibodies in MT-DAMPs in mitochondrial damage-associated molecular patterns (mtDAMPs), which are released into the blood from tissues damaged due to peripheral circulation disorders or from PBMCs stimulated by infectious agents, and by blocking the binding of the mtFP to FPR1, which is recycled within neutrophils and re-expressed on the surface of neutrophils, it restores the chemotaxis of neutrophils exposed to mtDAMPs and suppresses the occurrence of secondary nosocomial infections in sepsis patients recovering from the acute phase;

FIG. 4*a* relates to PMN calcium mobilization stimulated by 100 nM nicotinamide adenine dinucleotide dehydrogenase subunit-6 (ND6) and 100 nM N-formyl-methionine-leucine-phenylalanine (fMLF), that is FPR1 agonists. PMN calcium mobilization is inhibited by pretreatment with FPR1 antagonist (10 μM cyclosporine H, CsH). FIG. 4*b* relates to the area under the curve (AUC150) for 150 seconds of calcium depletion in the endoplasmic reticulum (ER) and the area under the curve (AUC) for 100 seconds of calcium influx (AUC100). ND6 and fMLF showed similar efficacy in inducing ER calcium depletion and subsequent calcium influx, but both were completely inhibited by 10 μM CsH pretreatment administered 1 minute before ND6 and fMLF treatment. Data are expressed as mean±standard error of three independent experiments;

FIG. 5*a* relates to PMN calcium mobilization stimulated by nicotinamide adenine dinucleotide dehydrogenase subunit-6 (ND6) and subsequent N-formyl-methionine-leucine-phenylalanine (fMLF). FIG. 5*b* quantifies the amount of ER calcium depletion stimulated by ND6 ($AUC_{150}$ primary) and fMLF ($AUC_{150}$ secondary), respectively, by calculating the area under the curve (AUC) over 150 seconds of endoplasmic reticulum (ER) calcium depletion. In order to quantify calcium influx, AUC over 100 seconds ($AUC_{100}$) was calculated. FIG. 5*c* relates to the chemotaxis of PMNs treated with ND6 in response to fMLF. 0.1% dimethyl sulfoxide (DMSO) was added to untreated PMNs (no tx). In order to determine the role of FPR1 in PMN chemotaxis, it was pretreated with 10 μM cyclosporine H (CsH) 15 minutes before incubation for PMN migration. ND6 treatment induced ER calcium depletion but dose-dependently inhibited fMLF-stimulated secondary ER calcium depletion and subsequent calcium influx. The ND6 treatment for PMNs also dose-dependently inhibited PMN chemotaxis in response to fMLF. The above results indicate that after FPR1 occupancy by ND6, fMLF binds to the remaining FPR1, causing calcium influx and PMN chemotaxis. Chemotaxis-related experiments were performed independently three times in four replicates. $^*P<0.05$. $^{}P<0.01$. $^{*}P<0.00$;

FIG. 7*a* relates to changes in PMN calcium mobilization after 30, 60 and 90 minutes after centrifugation ND6 removal. After 30 minutes of ND6 exposure, PMNs were centrifuged, and the supernatant was discarded. Next, the PMN pellet was resuspended in medium containing 0.1% DMSO (ND6-DMSO group) or medium containing ND6 (ND6-ND6 group). FIG. 7*b* relates to the AUC for 150 seconds of ER calcium depletion ($AUC_{150}$) and the AUC for 100 seconds of calcium influx ($AUC_{100}$). After 30 minutes of ND6 removal, ER calcium depletion was fully restored. In contrast to ER calcium depletion, calcium influx was still inhibited after 30 and 60 minutes, but was fully restored after 90 minutes of ND6 removal. FIG. 7*c* relates to changes in PMN chemotaxis after 30 and 90 minutes following centrifugation to remove ND6. PMN chemotaxis at 30 and 90 minutes was measured as the number of PMNs migrated during 60-minute incubation from 30 to 90 minutes and 90 to 150 minutes, respectively. Another group of PMNs was treated with 10 μM CsH 15 minutes prior to incubation to estimate the capacity of FPR1-mediated PMN chemotaxis. Consistent with calcium influx, PMN chemotaxis to fMLF was inhibited after 30 minutes following ND6 removal, but fully recovered after 90 minutes following ND6 removal. FIG. 7*d* relates to representative numerical values of flow cytometry detecting FPR1 in PMN membranes. FIG. 7*e* relates to mean fluorescence intensity (MFI) of flow cytometry. FPR1 expression on PMN membranes was fully restored after 30 minutes following ND6 removal. Data are expressed as mean±standard error of three independent experiments. Chemotaxis-related experiments were performed independently three times in four replicates. *P<0.05. P<0.01. *P<0.001;

FIG. 8*a* relates to the correlation between PMN chemotaxis and calcium mobilization steps in PMN sequentially stimulated by ND6 and fMLF. Correlation was analyzed by using Spearman's correlation coefficient (r). PMN chemotaxis was directly related to fMLF-induced ER calcium depletion ($AUC_{150}$ secondary) and subsequent calcium influx ($AUC_{100}$), but inversely related to ND6-induced ER calcium depletion ($AUC_{150}$ primary). FIG. 8*b* relates to the correlation of PMN following 30-minute ND6 exposure and 30 minutes after ND6 removal. FPR1 expression (MFI) was correlated with ER calcium depletion ($AUC_{150}$), but not correlated with calcium influx ($AUC_{100}$) and chemotaxis. FIG. 8*c* relates to the correlation of PMN following 30-minute ND6 exposure and 90 minutes after ND6 removal. FPR1 expression, ER calcium depletion, calcium influx and chemotaxis were correlated with one another. The above results indicate that recycled FPR1 was relocated to the PMN membrane immediately after the removal of circulating mtFP, but the recovery of calcium influx was delayed due to interfering molecules regulating the pathway from ER calcium depletion to calcium influx. *P<0.05. P<0.01. *P<0.001;

FIG. 11*a* relates to plasma ND levels after centrifugation following bead-anti-ND6 antibody treatment. FIG. 11*b* evaluates the level of ND6 removed by the bead-anti-ND6 antibody complex. The bead-anti-ND6 antibody treatment removed ND6 from plasma in a dose-dependent manner. An anti-ND6 antibody concentration of 4.0 μg/mL reduced plasma ND6 levels between 100 pM and 150 pM. 5.0 μg/mL was selected as the optimal antibody concentration for clinical application. Data are expressed as mean±standard error of three independent experiments;

FIG. 12*a* relates to mtFP levels in plasma obtained from septic shock patients on admission before and after the bead-anti-mtFP mixture treatment. FIG. 12*b* relates to the amount of mtFP removed by a bead-anti-mtFP mixture. The bead-anti-mtFP mixture successfully removed circulating mtFP from plasma obtained from septic shock patients. FIG. 12*c* relates to plasma cytokine and chemokine levels before and after the bead-anti-mtFP mixture treatment. In order to investigate the non-specific removal of cytokines and chemokines by the bead-anti-mtFP mixture, the levels of tumor necrosis factor (TNF)-α, interleukin (IL)-1β, IL-6, IL-10, growth regulatory oncogene (GRO)-α-induced IL-8 and leukotriene B4 (LTB4) were measured. The beads-anti-mtFP mixture did not significantly remove cytokines and chemokines. FIG. 12*d* relates to the effect of bead-anti-mtFP mixed treatment on the restoration of PMN chemotaxis. PMNs isolated from healthy volunteers were exposed to plasma obtained from septic shock patients for 30 minutes. Next, PMNs were resuspended in untreated plasma, plasma treated with a direct anti-mtFP cocktail or plasma treated with bead-anti-mtFP mixture and incubated for 90 minutes, and PMN chemotaxis was measured. Separate PMNs exposed to the bead-anti-mtFP mixture-treated plasma were pretreated with 10 μM CsH 15 minutes prior to the chemotaxis experiment. Unprocessed plasma from septic shock patients inhibited PMN chemotaxis from healthy volunteers in response to fMLF. Direct anti-mtFP antibody treatment could not restore PMN chemotaxis, but the bead-anti-mtFP mixture treatment significantly restored PMN chemotaxis. CsH-treated PMN chemotaxis exposed to untreated plasma was not significantly different from CsH-free PMN chemotaxis exposed to untreated plasma. The above results indicate that the structure of PMN chemotaxis through the bead-anti-mtFP cocktail treatment is primarily mediated by circulating mtFP and inhibiting recycled FPR1 occupancy. Data are expressed as mean±standard error of three independent experiments. ELISA was performed in duplicate. Chemotaxis-related experiments were performed independently three times in four replicates. *P<0.05. P<0.01.

Figure 1:
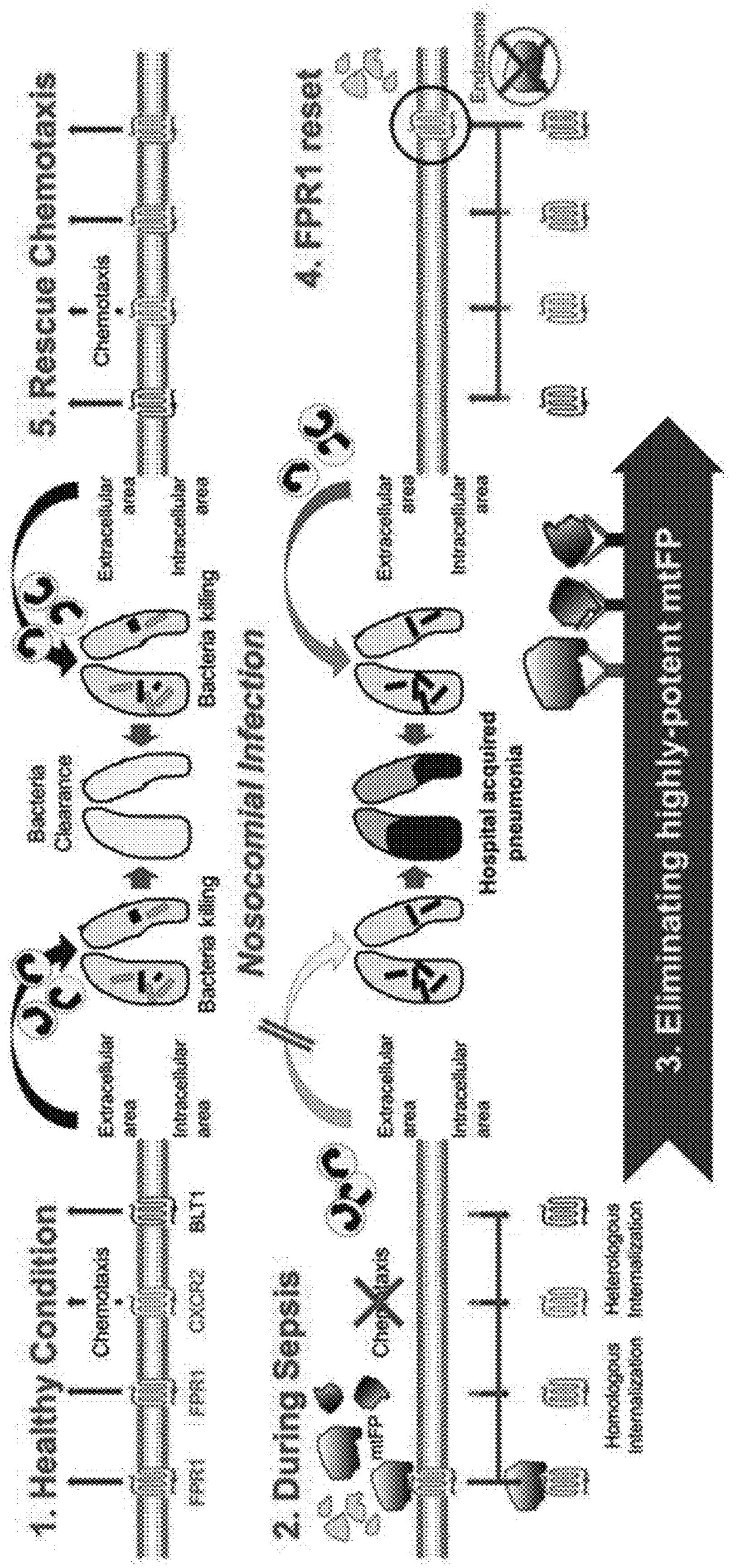
FIG. 1 relates to an overview of the present disclosure.
Figure 2:
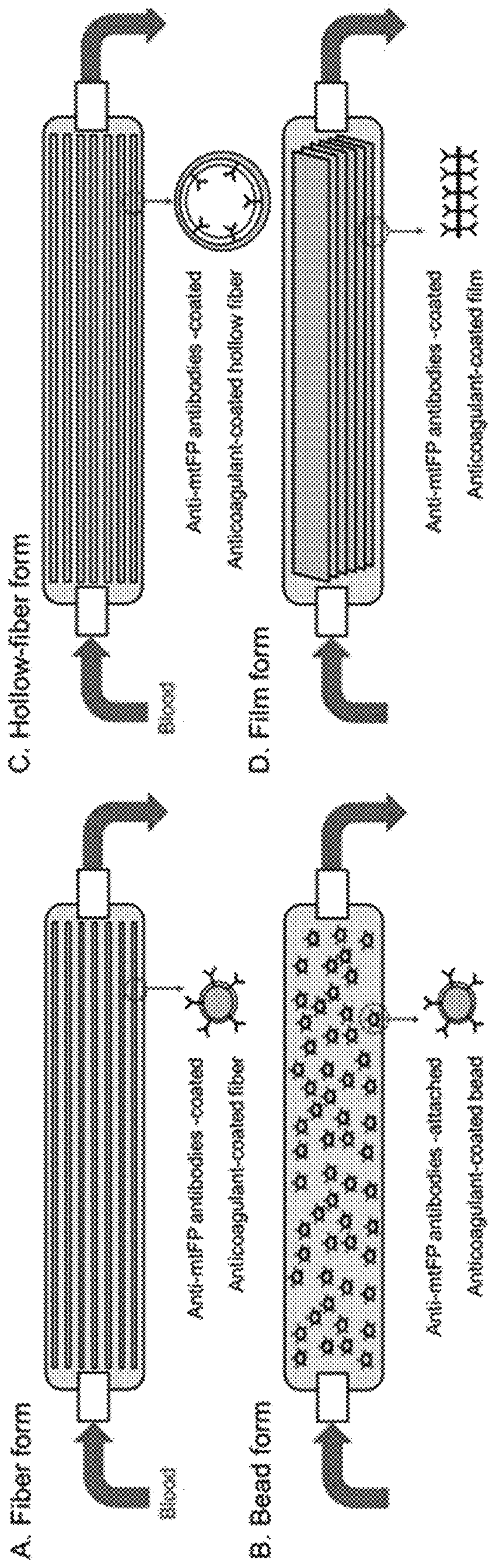
FIG. 2 relates to a blood perfusion device of the present disclosure. It is possible to remove target substances through extracorporeal blood perfusion with a blood perfusion device including an anti-mitochondrial N-formyl peptides antibody that is specific to mitochondrial NADH-ubiquinone oxidoreductase chain 6 (MT-ND6), MT-ND3, MT-ND4, MT-ND5 and mitochondrial cytochrome c oxidase 1 (MT-COX1). Blood perfusion equipment including anti-mtFP antibodies includes fiber form, bead form, film form, hollow-fiber form, and in addition to the above, it may include all cases of attaching or coating anti-mtFP antibodies to the blood contact area of various types of blood perfusion channels.

However, significant differences in chemotaxis were lost in PMNs obtained from septic shock patients who developed secondary infection and were exposed to bead-anti-mtFP mixture-treated plasma. Additional 50 μg/mL recombinant leukotriene B4 (LTB4) significantly restored PMN chemotaxis compared to PMN exposed to untreated plasma. The above results indicate that the bead-anti-mtFP mixture treatment can at least partially rescue PMN chemotaxis in septic shock patients with secondary infection and LTB4 may play an important role in the recovery of FPR-mediated PMN chemotaxis after the removal of circulating mtFP. Data are expressed as mean±standard error of three independent experiments. ELISAwas performed in duplicate. Chemotaxis-related experiments were performed independently three times in four replicates. *P<0.05. **P<0.01.

DETAILED DESCRIPTION OF EXEMPLARY EMBODIMENTS

Hereinafter, the present disclosure will be described in detail.

Unless otherwise defined, all technical and scientific terms used in the present specification have the same meaning as commonly understood by a person skilled in the art to which the present disclosure pertains. In general, the nomenclature used herein is well known and commonly used in the art.

Mitochondrial N-formyl peptide (mtFP), which is released into the blood from damaged tissues in sepsis patients, binds to formyl peptide receptor 1 (FPR1) on the surface of neutrophils (PMN) to suppress the chemotaxis of neutrophils against secondary invading bacteria such that it causes the progression of secondary infection in hospital by the invading bacteria. The mechanism is due to a decrease in receptors on the surface of neutrophils (homologous internalization) due to the intracellular movement of FPR1 bound to mtFP and a decrease in chemotactic receptors on the surface of neutrophils due to the accompanying intracellular movement of other chemotactic receptors (heterologous internalization).

The inventors of the present disclosure have confirmed in previous studies that the increased levels of circulating mtFP are independently associated with the development of secondary infections and 90-day mortality in patients recovering from septic shock, and increased susceptibility to secondary infection is mainly due to FPR1-mediated inhibition of neutrophil (PMN) chemotaxis, and it was confirmed that circulating mtFP does not affect the bactericidal activity of PMNs.

Furthermore, the inventors of the present disclosure confirmed that blocking FPR1 can preserve other chemokine receptors on PMN membranes by inhibiting the heterologous internalization of non-FPR1 chemokine receptors. However, in septic shock patients, FPR1 blocking may not be an effective treatment to rescue PMN chemotaxis to secondary infection sites.

As such, the inventors of the present disclosure hypothesized that removing circulating mtFP by an mtFP-specific antibody before redistributing recycled FPR1 to the PMN membrane would allow a sufficient amount of recycled FPR1 to bind to newly synthesized bacterial peptides, and accordingly established a hypothesis that PMN chemotaxis rescue would occur in response to secondary bacterial infection even in septic shock patients who developed secondary infection. Therefore, the inventors of the present disclosure investigated whether removing circulating mtFP from plasma via mtFP-specific antibodies can rescue FPR1-mediated PMN chemotaxis against secondary bacterial infection in patients recovering from septic shock who developed secondary infection.

Figure 10:
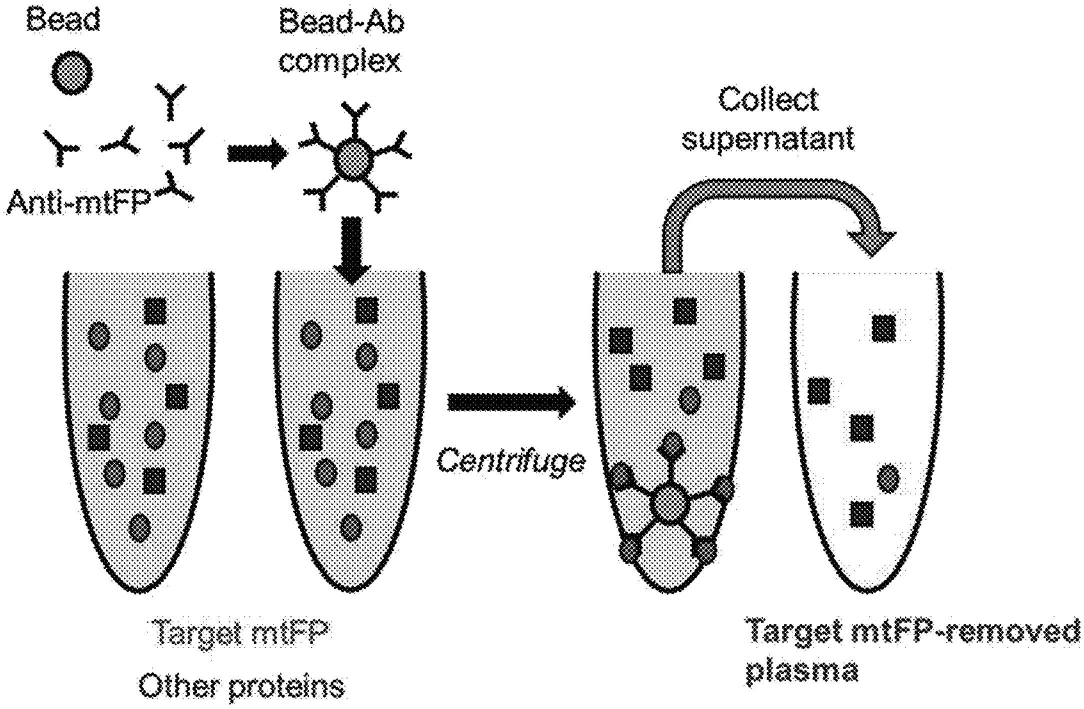
FIG. 10 relates to a bead-antibody complex combining protein A/sepharose and an antibody specific to mitochondrial N-formyl peptide (mtFP). The bead-anti-mtFP antibody complex was administered to the plasma of a septic shock patient and then centrifuged to successfully remove the target mtFP from the plasma.
Figure 11A:
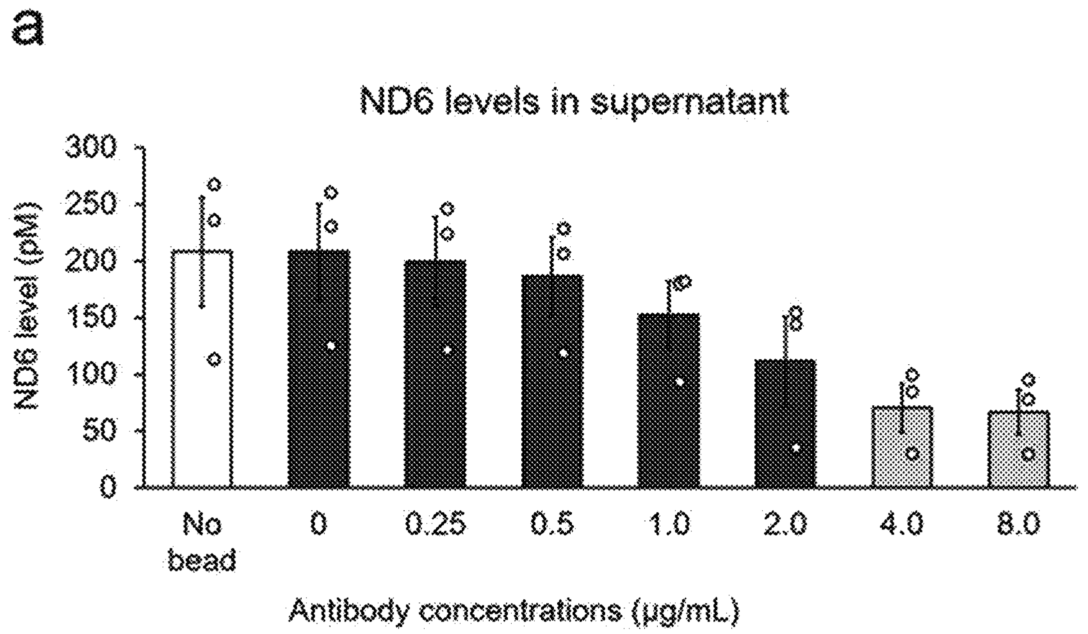
FIGS. 11*a* and 11*b* relate to ND6 removal through bead-anti-ND6 antibody treatment in plasma obtained from septic shock patients.
Figure 11B:
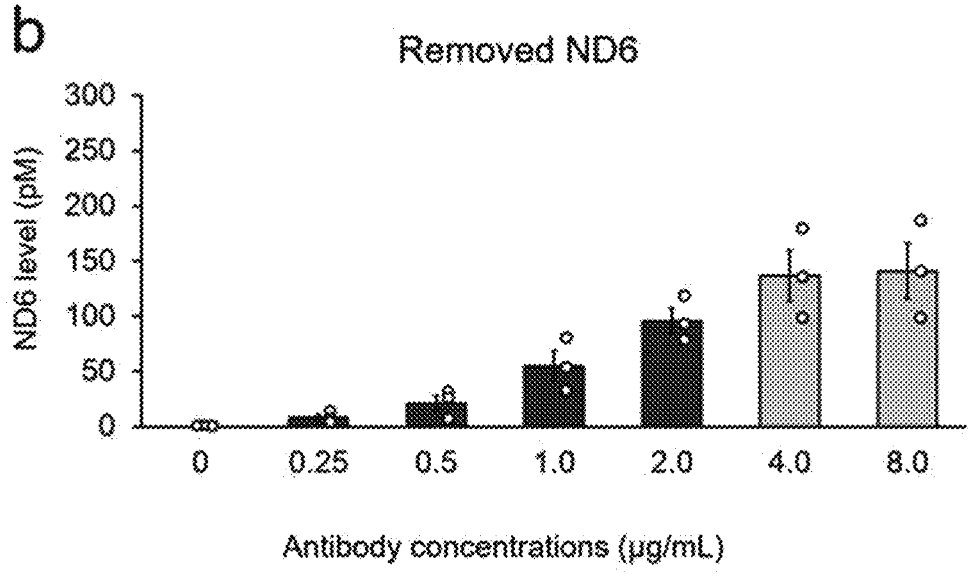

First of all, in order to determine the effect of antibody treatment specific for mitochondrial NADH-ubiquinone oxidoreductase chain 6 (MT-ND6), MT-ND3, MT-ND4, MT-ND5 and mitochondrial cytochrome c oxidase 1 (MT-COX1), plasma from sepsis patients was separated, and changes in the chemotaxis of neutrophils from normal people and sepsis patients exposed to the same were measured. There was no therapeutic effect when the existing anti-mtFP antibody was administered directly to plasma. In other words, previously, it was confirmed that anti-mtFP antibodies have no therapeutic effect when administered directly because they do not block FPR1 binding to the N-terminal of mtFP. As such, it was confirmed whether mtFP in the blood can be removed when beads and antibodies are combined and then removed by centrifugation. As a result, when beads and 4 anti-mtFP specific antibodies were combined and administered to the plasma of a sepsis patient, it was confirmed that mtFP can be effectively removed from the blood (FIGS. 10-11*b*). However, the bead-antibody complex has a large molecular weight and is expected to cause many side effects when administered into the body, and thus, there is a problem that it cannot be administered directly into the body. As such, when an extracorporeal circulation membrane filter using a bead-antibody complex or other type of antibody binding material is fabricated to perform blood perfusion outside the body, foreign substances will not be able to enter the body, and thus, mtFP can be safely removed from the blood. When neutrophils from sepsis patients were isolated and exposed to plasma from which 4 blood mtFPs (ND6, ND3, ND4, ND5) were removed, it was confirmed that the chemotaxis of neutrophils was restored (FIGS. 12*a*-13*d*). This indicates that the removal of target substances (FIGS. 12*a*-13*d*) is possible through extracorporeal blood perfusion with a blood perfusion device including existing antibodies that are specific for 4 or 5 mitochondrial formyl peptides, and it may be possible to restore the chemotaxis of neutrophils to the site of secondary bacterial infection and thereby suppress the progression of systemic secondary infection in hospital.

FPR1 bound to mtFP enters the cell, removes mtFP from the endosome, and is recycled back to the neutrophil surface for expression. Therefore, by blocking the recombination of mtFP in the blood to FPR1 expressed on the surface of neutrophils, it promotes the movement of neutrophils to the site of secondary bacterial infection, so as to eliminate the secondary invading bacteria and suppress the progression to systemic secondary infection (FIG. 1).

As used herein, the term "perfusion" refers to the flow of fluid to organs or body tissues through the circulatory or lymphatic system, and especially refers to the delivery of blood to the capillaries within the tissues.

As used herein, the term "anti-mtFP antibody" (anti-mitochondrial N-formyl peptides antibody) is also referred to as a mitochondrial N-formyl peptide (mtFP) specific antibody, and it may remove mitochondrial N-formyl peptide (mtFP) included in blood through the mtFP-specific antibody. By removing the mtFP, the binding of the mtFP to the formyl peptide receptor 1 (FPR1) of the PMN membrane may be blocked, and it is possible to restore the chemotaxis of polymorphonuclear leukocytes (PMN). The mtFP may be characterized as being released into the blood from peripheral blood mononuclear cells (PBMCs) stimulated by damaged tissues and infectious agents.

As used herein, the term "adsorption medium" refers to a substance to which cells, organisms, viruses, toxins, pathogens, polypeptides, polynucleotides, chemical molecules, small molecules, biological molecules or fragments thereof can be attached to the surface thereof.

In one aspect, the present disclosure relates to a blood perfusion device, including a blood inlet for allowing blood to flow into the device; an adsorption medium including an anti-mitochondrial N-formyl peptides antibody (anti-mtFP antibody); and a blood outlet for allowing blood to flow out of the device.

In the present disclosure, the blood perfusion device may suppress the occurrence of secondary infection in hospital. Therefore, the blood perfusion device can be used for patients whose symptoms and clinical outcomes may worsen due to secondary infection in the hospital.

In the present disclosure, a target subject of the blood perfusion device may be characterized as at least one selected from the group consisting of sepsis patients, septic shock patients, severe trauma patients, organ transplant patients, hemorrhagic shock patients, myocardial infarction patients, cardiogenic shock patients, stroke patients and patients surviving after cardiac arrest, but the present disclosure is not limited thereto, and the blood perfusion device may be used for patients who require hospitalization for a considerable period of time even after acute treatment.

In the present disclosure, the mtFP may be characterized as at least one selected from the group consisting of mitochondrial NADH-ubiquinone oxidoreductase chain 6 (MT-ND6), MT-ND3, MT-ND4, MT-ND5 and mitochondrial cytochrome c oxidase 1 (MT-COX1), but the present disclosure is not limited thereto.

In the present disclosure, the blood perfusion device may remove blood from a subject and add desired substances such as, but not limited to, oxygen, blood-anticoagulant, anesthetic and the like to the blood before returning the same to the subject. Additionally, unwanted substances such as naturally occurring toxins or poisons may be removed from the blood.

In the present disclosure, the blood perfusion device may further include oxygen, a blood-anticoagulant and leukotriene B4 (LTB4), and the leukotriene B4 (LTB4) may be included at a concentration of 10 to 100 pg/mL.

In the present disclosure, the anti-mtFP antibody may be included at a concentration of 0.5 to 20.0 μg/mL, preferably, 1.0 to 15.0 μg/mL, more preferably, 2.0 to 10.0 μg/mL, and most preferably, 4.0 to 8.0 μg/mL, but the present disclosure is not limited thereto, but if the anti-mtFP antibody is included at a concentration of less than 0.5 μg/mL and/or more than 20.0 μg/mL, it may not effectively remove mtFP from the blood or may cause side effects.

In the present disclosure, the adsorption medium may have an anti-mtFP antibody attached or coated on the surface thereof. The adsorption medium may include fiber form, bead form, film form, hollow-fiber form and the like, but the present disclosure is not limited thereto, and it may also include various forms that attach or coat the anti-mtFP antibody to the blood contact site.

In the present disclosure, the blood perfusion device may be connected to a hemodialysis device, a continuous renal replacement therapy (CRRT) device, an extracorporeal membrane oxygenation (ECMO) device or other various extracorporeal circulation devices to perform blood perfusion, but the present disclosure is not limited thereto.

In another aspect, the present disclosure provides an in vitro method for reducing secondary infection in hospital, including the following steps:

(a) passing blood obtained from a subject through a device comprising an adsorption medium comprising an anti-mitochondrial N-formyl peptides antibody (anti-mtFP antibody);
(b) producing blood with a reduced level of mtFP in the blood; and
(c) injecting the blood with a reduced mtFP level into the subject.

In the present disclosure, the subject may be characterized as at least one selected from the group consisting of sepsis patients, septic shock patients, severe trauma patients, organ transplant patients, hemorrhagic shock patients, myocardial infarction patients, cardiogenic shock patients, stroke patients and patients surviving after cardiac arrest, but the present disclosure is not limited thereto, and the above method may be used for patients who require hospitalization for a considerable period of time even after acute treatment.

In the present disclosure, the mtFP may be characterized as at least one selected from the group consisting of mitochondrial NADH-ubiquinone oxidoreductase chain 6 (MT-ND6), MT-ND3, MT-ND4, MT-ND5 and mitochondrial cytochrome c oxidase 1 (MT-COX1), but the present disclosure is not limited thereto.

In the present disclosure, the anti-mtFP antibody may be included at a concentration of 0.5 to 20.0 μg/mL, preferably, 1.0 to 15.0 μg/mL, more preferably, 2.0 to 10.0 μg/mL, and most preferably, 4.0 to 8.0 μg/mL, but the present disclosure is not limited thereto, but if the anti-mtFP antibody is included at a concentration of less than 0.5 μg/mL and/or more than 20.0 μg/mL, it may not effectively remove mtFP from the blood or may cause side effects.

In the present disclosure, the adsorption medium may be characterized by having an anti-mtFP antibody attached or coated on the surface thereof. The adsorption medium may include fiber form, bead form, film form, hollow-fiber form and the like, but the present disclosure is not limited thereto, and it may also include various forms that attach or coat the anti-mtFP antibody to the blood contact site.

Hereinafter, the present disclosure will be described in more detail through examples. These examples are only for illustrating the present disclosure, and it is apparent to those skilled in the art that the scope of the present disclosure should not be construed as limited by these examples.

Example 1

Experimental Materials and Methods

(Example 1-1) Ethics

The collection of blood samples from healthy volunteers and septic shock patients was approved by the Institutional Review Board (IRB) of Seoul National University College of Medicine/Seoul National University Hospital (IRB number: 1605-044-760). The Clinical Data Repository Protocol for Patients with Septic Shock has also been approved by the IRB (IRB number: 1707-012-865) and registered at ClinicalTrials.gov (NCT01670383). Additionally, written consent was obtained from healthy volunteers, patients with septic shock or legally authorized representatives.

(Example 1-2) Information on Septic Shock Patients

The inventors of the present disclosure selected sepsis patients who visited the emergency room based on a qSOFA (quick sequential organ failure assessment) score of 2 or higher. Afterwards, the inventors of the present disclosure calculated the SOFA score and injected 30 mL/kg crystalloid if the score was 2 or more. Patients were diagnosed with septic shock if the mean arterial pressure (MAP) was less than 65 mmHg and the serum lactate level was more than 2 mmol/L despite a crystalloid infusion of 30 mL/kg. Patients who were diagnosed with septic shock received a continuous intravenous infusion of vasopressors to maintain MAP above 65 mmHg, and after collecting blood samples for incubation studies, broad-spectrum antibiotics were administered intravenously within 1 hour, and the patients were admitted to the intensive care unit as soon as possible. Demographic and laboratory data were collected from patients who were admitted to the intensive care unit.

(Example 1-3) Human PMN Isolation and Cell-Free Plasma

Human polymorphonuclear cells (PMN) were isolated according to the following method. Heparinized (10 U/mL) whole blood samples collected from healthy volunteers and patients with septic shock were centrifuged at 200 g for 10 minutes at 4° C. The plasma layer was obtained and centrifuged again at 20,000 g for 10 minutes at 4° C. to obtain a supernatant (cell-free plasma).

5 mL of buffy coat and red blood cells overlaid on 5 mL of 1-Step™ polymorph (AN221725, Accurate Chemical, Westbury, NY) were centrifuged at 550 g for 30 minutes at 24° C., and the PMN layer was collected separately. In order to restore the osmotic pressure, an equal volume of ice-cold 0.45% sodium chloride (NaCl) was mixed for 5 minutes. After washing with Roswell Park Memorial Institute (RPMI)-1640 medium (11875093, Thermo Fisher, Waltham, MA), the remaining red blood cells were lysed in 20 mL of ice-cold 0.2% NaCl for 20 s, and then, 20 mL of ice-cold 1.6% NaCl was administered. After centrifugation at 200 g for 10 minutes at 4° C., the supernatant was discarded.

(Example 1-4) MTFP

The hexapeptide of ND6 (N-formyl-methionine-methionine-tyrosine-alanine-leucine-phenylalanine, N-formyl-MMYALF), ND3 (N-formyl-methionine-asparagine-phenylalanine-alanine-leucine-isoleucine, N-formyl-MNFALI), ND4 (N-formyl-methionine-leucine-lysine-leucine-isoleucine-valine, N-formyl-MLKLIV), and ND5 (N-formyl-methionine-threonine-methionine-histidine-threonine-threonine, N-formyl-MTMHTT) was synthesized by requesting at Peptron (Daejeon, Korea). N-formyl-methionine-leucine-phenylalanine (fMLF, standard bacterial FP) was purchased from Sigma-Aldrich (f506, St. Louis, MO).

(Example 1-5) Calcium Mobilization within PMN Cells

Calcium mobilization within PMN cells was measured according to the following method. The separated PMN pellet was resuspended in pH 7.4 hydroxyethyl piperazine ethane sulfonic acid (HEPES) buffer solution. This HEPES buffer solution includes 20 mM HEPES, 140 mM NaCl, 5 mM potassium chloride (KCl), 1 mM magnesium chloride ($MgCl_2$), 1 mM calcium chloride ($CaCl_2$)), 10 mM glucose and 0.1% bovine serum albumin (BSA, A2058 Sigma-Aldrich). PMNs were loaded with fura2-AM (F1221, Thermo Fisher, Waltham, MA) for 45 minutes at 37° C.

Fluorescence was measured at 505 nm with 340/380 nm dual-wavelength excitation at 37° C. by using a spectrofluorometer (FluoroMax Plus-C, Horiba, Ltd., Kyoto, Japan). For the quantitative measurement of endoplasmic reticulum (ER) calcium depletion, PMNs were centrifuged at 200 g for 10 minutes at 4° C. PMN pellets were then resuspended in a calcium-free HEPES buffer solution including 0.3 mM ethylene glycol-bis(2-aminoethylether)-N,N,N',N'-tetraacetic acid (EGTA, E3889, Sigma-Aldrich, St. Louis, MO), and stimulated with ND6 and fMLF or with ND6 alone. 0.1% dimethyl sulfoxide (DMSO) was added to the medium without ND6 or fMLF. After endoplasmic reticulum calcium was depleted, 1.8 mM $CaCl_2$) was added to induce cytoplasmic calcium influx. Endoplasmic reticulum calcium depletion and calcium influx were assessed by measuring the 340 nm/380 nm ratio and quantified as AUC over 150 seconds ($AUC_{150}$) and AUC over 100 seconds ($AUC_{100}$), respectively. The role of FPR1 in calcium mobilization was determined by pretreatment with 10 μM CsH 1 minute prior to the induction of endoplasmic reticulum calcium depletion. Three independent experiments were performed.

(Example 1-6) PMN Chemotaxis

PMN chemotaxis was assessed by using multiScreen 96-well plates consisting of a 3-μm pore membrane (MAMIC3S10, Merck Millipore, Darmstadt, Germany). After preplanned treatment with ND6 or patient plasma, isolated human PMNs were centrifuged at 200 g for 10 minutes at 4° C. Afterwards, the PMN pellet was resuspended in Dulbecco's modified Eagle medium (DMEM, 11885-084, Thermo Fisher) containing 10% fetal bovine serum (FBS, F2442, Sigma-Aldrich). Before use, FBS was inactivated by heating at 56° C. for 1 hour. PMNs were placed in the upper chamber of the plate ($0.1\times10^6$ PMNs at 75 μL per well), and medium containing 100 nM fMLF was placed in the lower chamber (150 μL per well). In medium without ND6 or fMLF, 0.1% DMSO was added.

Plates were incubated for 60 minutes in an incubator at 37° C. with 5% carbon dioxide ($CO_2$). In order to determine the role of FPR1 in PMN chemotaxis, 10 μM CsH was added to one group of PMNs 15 minutes prior to incubation. After 60 minutes of incubation, the upper and lower chambers of the plate were separated, and the medium in the lower chamber was transferred to a 1.5 mL-Eppendorf (EP) tube. The EP tube was centrifuged at 500 g for 5 minutes at 4° C., and the supernatant was aspirated. The pellet was resuspended in 200 μL of distilled water including a lysis buffer solution (1:20 dilution) and CyQuant GR dye (1:400 dilution, C7026, Thermo Fisher). PMNs were vortexed and dissolved for 15 minutes at room temperature in the dark. Afterwards, the contents were transferred to a 96-well plate, and fluorescence was measured at an excitation/emission wavelength of 480/520 nm with a cut-off of 515 nm. The number of migrated PMNs was calculated by using a standard curve derived from known PMN numbers. A 4-well replicate experiment was performed for each experimental group, and three independent experiments were performed.

(Example 1-7) Flow Cytometry

The purity of isolated human PMNs was assessed by flow cytometry using a BD FACSCalibur (BD Biosciences, San Jose, CA). Human bone marrow cells were sorted by using fluorescein (FITC)-conjugated anti-human CD15 antibody (301903, BioLegend, San Diego, CA). Among these cells, CD49d negative and CD16 positive cells were counted as PMN. Phycoerythrin/cyanine 7 (PE/Cy7)-conjugated anti-human CD49d antibody (304313, BioLegend) and allophycocyanin (APC)-conjugated anti-human CD16 antibody (360705, BioLegend) were used.

FPR1 expression on PMN membranes and the amount of CaMK2 in the homogenized PMN pellet were also detected by flow cytometry. In order to detect FPR1 on PMN membranes, PMNs ($1.0\times10^6$ in 200 μL) were incubated with FITC-conjugated anti-human FPR1 antibody (2 μL, FAB3744F, R&D Systems, Minneapolis, MN) for 30 minutes at room temperature in the dark. FITC-conjugated mouse IgG2a, κ isotype control antibody (400210, BioLegend, San Diego, CA) was used as a negative control. After washing twice, fluorescence was measured. APC-conjugated anti-CaMK2 antibody (2 μL, ab225178, Abcam, Cambridge, UK) was used to detect the amount of CaMK2 in 200 μL of homogenized PMN pellet obtained by homogenization of $1.0\times10^6$/1 mL PMN for 30 seconds at 4° C. and centrifugation at 20,000 g for 10 minutes. FPR1 expression in PMN membranes and the amount of CaMK2 in homogenized PMN pellets were quantified as mean fluorescence intensity (MFI) by using FlowJo version 10.0 (FlowJo, LLC, Ashland, OR). At least three independent experiments were performed.

(Example 1-8) Enzyme-Linked Immunosorbent Assay (ELISA)

CaMK2 levels in the supernatants of homogenized PMNs obtained by homogenization of $1.0\times10^6$/1 mL PMN for 30 seconds at 4° C. and centrifugation at 20,000 g for 10 minutes were measured by using the human calcium/calmodulin-dependent protein kinase II (CAMK2) ELISA kit (MBS005464, MyBioSource, San Diego, CA) according to the manufacturer's instructions.

Plasma ND6, ND3, ND4 and ND5 levels were respectively measured by using human NADH ubiquinone oxidoreductase chain 6(MT-ND6) ELISA Kit(MBS7246296, MyBioSource), human NADH ubiquinone oxidoreductase chain 3(MT-ND38) ELISA Kit (MBS7244982, MyBioSource), human NADH ubiquinone oxidoreductase chain 4(MT-ND4) ELISA Kit (MBS9715152, MyBioSource) and human NADH ubiquinone oxidoreductase chain 5(MT-ND5) ELISAKit (MBS7236655, MyBioSource).

Plasma tumor necrosis factor (TNF)-α, interleukin (IL)-1β, IL-6 and IL-10 levels were respectively measured by using the TNF alpha beta human ELISAKit (KHC3011, Thermo Fisher), IL-1 beta human ELISA Kit(KHCOO11, Thermo Fisher), IL-6 human ELISA Kit (KHCO061, Thermo Fisher) and IL-10 human ELISA Kit (KHCO101, Thermo Fisher). The plasma growth regulated oncogene (GRO)-α, IL-8 and leukotriene B4 (LT B4) levels were respectively measured by using the GRO alpha (CXCL1) human ELISA Kit (BMS2122, Thermo Fisher), IL-8 human ELISA Kit (KHCO081, Thermo Fisher) and LTB4 parameter analysis kit (KGE006B, R&D Systems, Minneapolis, MN). All experiments were performed in duplicate.

(Example 1-9) Centrifugal Removal of ND6

Isolated human PMNs obtained from healthy volunteers in DMEM containing 10% FBS (control medium) were treated with 100 nM of ND6 for 30 minutes on a 10-rpm rotator at 37° C. After centrifugation at 200 g for 10 minutes, the supernatant was discarded. PMN pellets were resuspended in 100 nM ND6 treatment medium (ND6-ND6 group) or control medium (ND6-DMSO group). 0.1% DMSO was added to the control medium without ND6. Next, PMNs were incubated at 37° C. for 90 minutes on a 10-rpm rotator. For calcium mobilization experiments, PMNs were extracted from the ND6-ND6 and ND6-DMSO groups at 30, 60 and 90 minutes, respectively. For chemotaxis experiments, PMNs were extracted at 30 and 90 minutes.

(Example 1-10) Estimation of Required Anti-ND6 Antibody Dose

Commercial polyclonal anti-ND6 antibody (orb6548) was purchased from Biorbyt Ltd. (Cambridge, UK). Protein A Sepharose® was purchased from Abcam (ab193256). First of all, 0.125 μg/mL, 0.25 μg/mL, 0.5 μg/mL, 1.0 μg/mL or 2.0 μg/mL of the anti-ND6 antibody was directly administered to plasma obtained from a septic shock patient through an arterial catheter. After 2 hours of incubation on a 10-rpm rotator at 37° C., the plasma containing the anti-ND6 antibody was centrifuged at 20,000 g for 10 minutes at 4° C., and the supernatant was obtained. Afterwards, plasma ND6 levels were measured by ELISA.

The inventors of the present disclosure prepared a beads-anti-ND6 antibody complex. 80 μL of Protein A Sepharose® was washed twice with phosphate-buffered saline (PBS, pH 7.4, 10010023, Thermo Fisher) and co-incubated with the anti-ND6 antibody at 0.25 μg/mL, 0.5 μg/mL, 1.0 μg/mL, 2.0 μg/mL, 4.0 μg/mL or 8.0 μg/mL for 4 hours on a 10-rpm rotator at 4° C. The bead-anti-ND6 antibody complex was centrifuged at 3,000 g for 2 minutes at 4° C., and the supernatant was discarded. After washing twice with 3,000 g of PBS for 2 minutes at 4° C., the bead-anti-ND6 antibody complex was co-incubated with 500 μL plasma obtained from a septic shock patient via an arterial catheter for 2 hours on a 10-rpm rotator at 37° C. The bead-anti-ND6 antibody complex that could be attached by circulating ND6 was removed by centrifugation at 20,000 g for 10 minutes at 4° C., and the supernatant was obtained. Plasma ND6 levels before and after the bead-anti-ND6 antibody complex treatment were measured by ELISA. Three independent experiments were performed, and ELISA was performed in duplicate.

(Example 1-11) Preparation of Beads-Anti-mtFP Cocktail

In addition to the anti-ND6 antibody, commercially available polyclonal anti-ND3 (orb185335), anti-ND4 (orb546348) and anti-ND5 (orb6547) antibodies were purchased from Biorbyt Ltd. Based on experimental results that estimated the required anti-ND6 antibody dose (5.0 μg/mL with 80 μL beads in 500 μL plasma), 5.0 μg/mL of each antibody specific for ND6, ND3, ND4, and ND5 was co-incubated with 320 μL beads for 4 hours on a 10-rpm rotator at 4° C. After washing twice with PBS, 500 μL plasma was added to the bead-anti-mtFP antibody complex (bead-anti-mtFP mixture) and co-incubated for 2 hours at 37° C. on a 10-rpm rotator. Next, plasma containing the bead-anti-mtFP mixture was centrifuged at 20,000 g for 10 minutes at 4° C., and the supernatant was obtained. Plasma ND6, ND3, ND4 and ND5 levels were measured by ELISA before and after the bead-anti-mtFP mixture treatment. Plasma TNF-α, IL-10, IL-6, IL-10, GRO-α, IL-8 and LTB4 levels were also measured. Plasma obtained from healthy volunteers was used as a negative control group.

The effect of bead-anti-mtFP mixture treatment on PMN chemotaxis rescue was analyzed. PMS was isolated from blood samples obtained from healthy volunteers and exposed to untreated plasma from septic shock patients for 30 minutes in a 10-rpm rotator at 37° C. After centrifugation at 200 g for 10 minutes at 4° C., the supernatant was discarded. PMN pellets were resuspended in untreated plasma or bead-anti-mtFP mixture-treated plasma and incubated for 90 minutes on a 10-rpm rotator at 37° C. Next, PMN chemotaxis to 100 nM fMLF was measured. In order to estimate the capacity of non-FPR1-mediated PMN chemotaxis, separate PMNs exposed to bead anti-mtFP mixture-treated plasma were pretreated with 10 μM CsH 15 minutes prior to the chemotaxis experiment. A 4-well replicate experiment was performed for each experimental group, and three independent experiments were performed.

(Example 1-12) PMN Chemotaxis Rescue in Septic Shock Patients with Secondary Infection Before the experiment, 320 μL of protein A Sepharose® was washed twice with PBS and co-incubated with 5.0 μg/mL of each antibody specific for ND6, ND3, ND4 and ND5 for 4 hours at 4° C. on a 10-rpm rotator. Blood samples were collected between days 10 and 14 of hospitalization through an arterial catheter from patients with septic shock who were aware of secondary infection or from patients with septic shock who did not develop secondary infection. Immediately after blood collection, plasma was separated, and cell-free plasma was prepared. Half of the plasma was divided into 500 μL per EP tube and incubated with the bead-anti-mtFP mixture for 2 hours on a 10-rpm rotator at 37° C. The other half of the plasma was incubated without the bead-anti-mtFP mixture. Plasma obtained from patients negative for secondary infection was also incubated without the bead-anti-mtFP mixture. The levels of ND6, ND3, ND4 and ND5 in the plasma of septic shock patients who developed secondary infection and in the plasma of patients negative for secondary infection were measured by ELISA before and after treatment with the bead anti-mtFP mixture. Plasma TNF-α, IL-1, IL-6, IL-10, GRO-α, IL-8 and LTB4 levels were also measured.

PMNs from the patients were isolated during a 2-hour plasma incubation period. After this preparation, PMNs were exposed to plasma untreated with the bead-anti-mtFP mixture for 30 minutes on a 10-rpm rotator at 37° C. After centrifugation at 220 g for 10 minutes at 4° C., the supernatant was discarded. PMN pellets were resuspended in the bead-anti-mtFP mixture untreated plasma or bead-anti-mtFP mixture treated plasma and incubated for 90 minutes at 37° C. on a 10-rpm rotator. Next, PMN chemotaxis to 100 nM fMLF was measured. In order to investigate the role of LTB4 in the recovery of FPR1-mediated PMN chemotaxis after the removal of circulating mtFP, at the start of the incubation for PMN migration, 50 μg/mL of recombinant LTB4 (L0517, Sigma Aldrich) was added to separate PMNs exposed to bead-anti-mtFP mixture-treated plasma. A 4-well replicate experiment was performed for each experimental group, and three independent experiments were performed.

(Example 1-13) Statistics

Data were analyzed by using one-way analysis of variance with Tukey's post hoc test. At least three independent experiments were performed. A p-value of less than 0.05 was considered statistically significant (significance level: two-sided test). Statistical analyzes were performed by using IBM SPSS version 27.0 for Windows (SPSS, Chicago, IL).

Example 2

FPR1-Mediated Calcium Mobilization and PMN Chemotaxis

Figure 3:
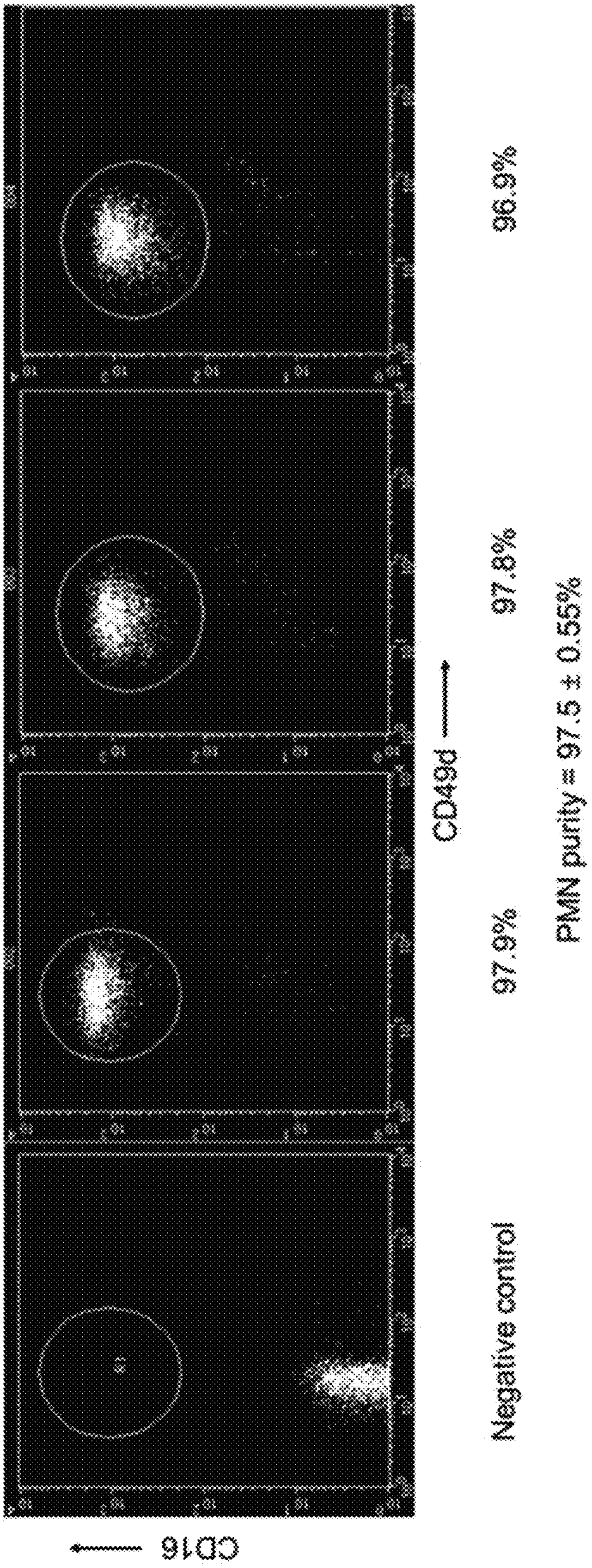
FIG. 3 relates to the purity of isolated human polymorphonuclear cells (PMN) determined by flow cytometry. The average purity of PMNs isolated from three independent experiments was 97.53±0.55% (standard deviation)
Figure 4A:
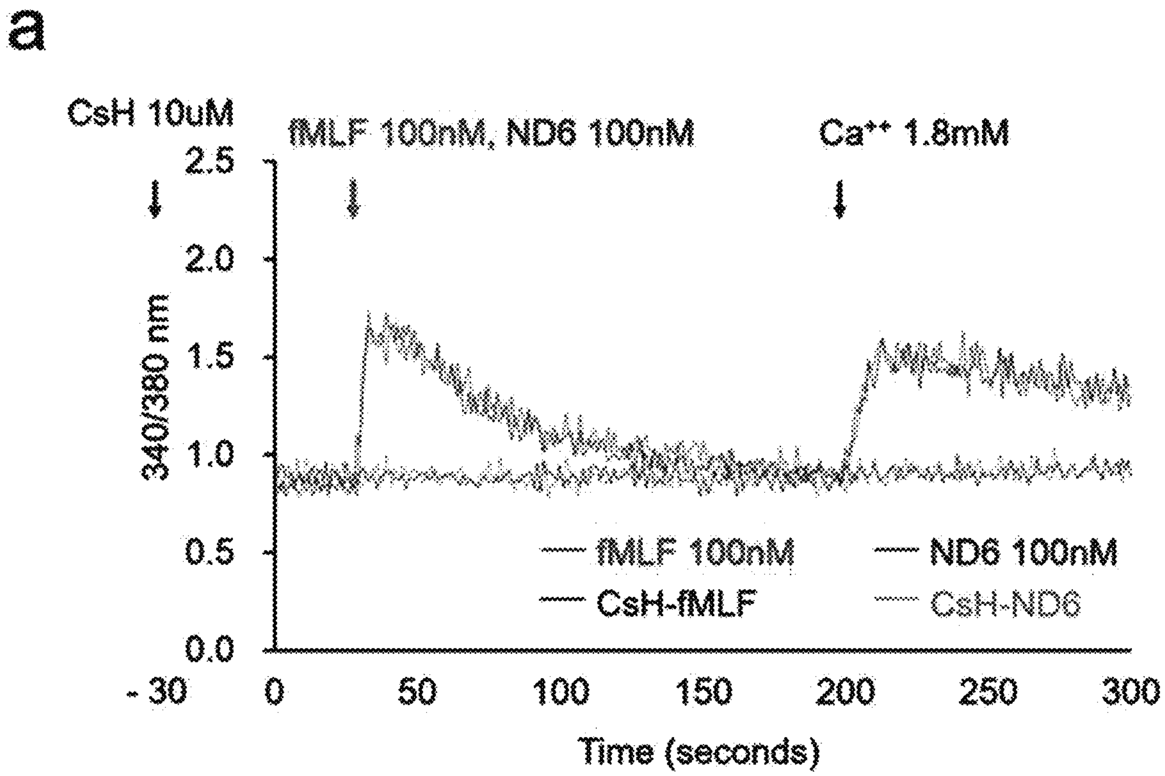
FIGS. 4*a* and 4*b* relate to formyl peptide receptor 1 (FPR1) agonists and antagonists.
Figure 4B:
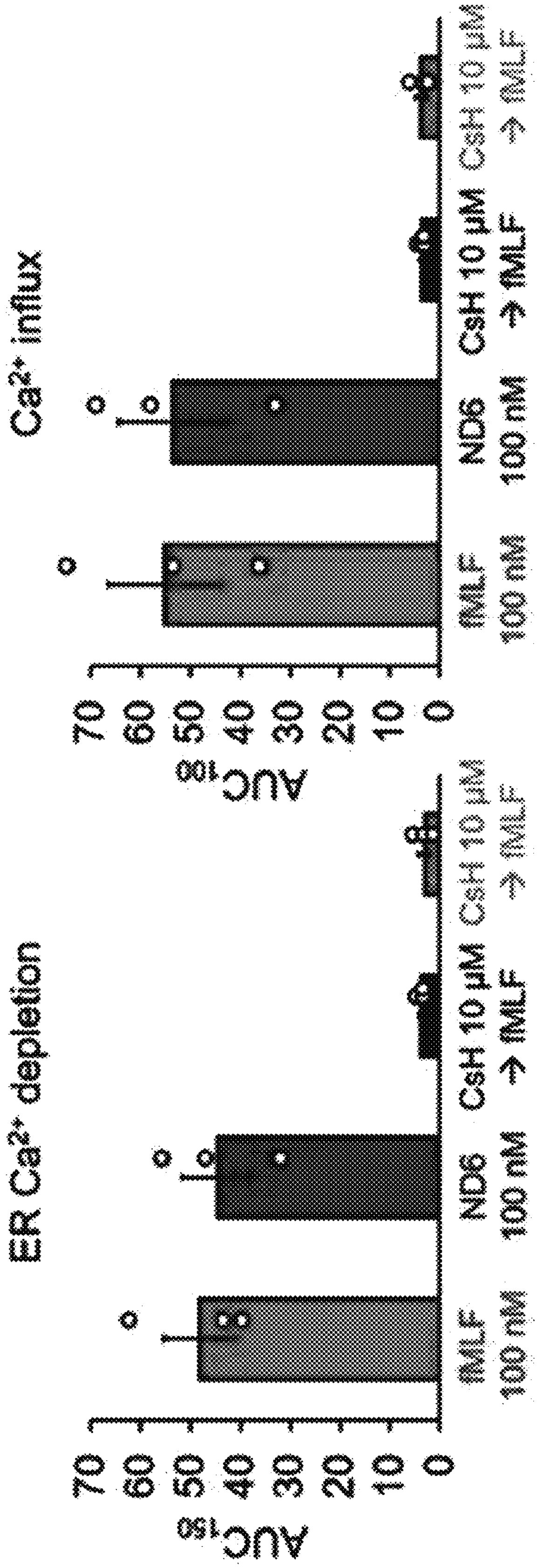

In order to investigate which steps of intracellular calcium mobilization stimulated by FPR1 agonists directly correlate with PMN chemotaxis, the inventors of the present disclosure quantitatively measured the amounts of endoplasmic reticulum (ER) calcium depletion and subsequent calcium influx into the cytoplasm in isolated human PMNs obtained from healthy volunteers. The average purity of PMNs isolated from three independent experiments was 97.5% (FIG. 3). In order to simulate an environment in which secondary infection occurs in the presence of circulating mtFP, 100 nM, 10 nM, 5 nM and 0 nM of ND6 were treated for 30 seconds, and 100 nM of N-formyl-methionine-leucine-phenylalanine (fMLF, standard bacterial FP) was treated for 200 seconds in calcium-free conditions. Among the 13 human mtFPs, ND6 is known to be the most potent human mtFP in stimulating ER calcium depletion and PMN chemotaxis, followed by ND3, ND4 and ND5. The area under the curve (AUC) of ER calcium depletion over 150 seconds was calculated to quantify the amount of ER calcium depletion stimulated by ND6 ($AUC_{150}$ primary) and fMLF ($AUC_{150}$ secondary), respectively. Calcium influx through SOCE (store-operated calcium entry) was quantified by treating 1.8 mM calcium chloride ($CaCl_2$)) for 380 seconds and calculating the AUC ($AUC_{100}$) for 100 seconds. The potency of 100 nM ND6 and 100 nM fMLF to induce ER calcium depletion and the FPR1 antagonistic effect of 10 μM cyclosporine H (CsH, an FPR antagonist) were tested before the experiment (FIGS. 4A and 4B). ND6 and fMLF showed similar efficacy in inducing ER calcium depletion and subsequent calcium influx, but both were completely inhibited by 10 μM CsH pretreatment 1 minute prior to ND6 and fMLF treatment. In previous studies, the inventors of the present disclosure confirmed that 100 nM was the most potent concentration of fMLF to induce FPR1-mediated PMN chemotaxis and 10 μM CsH completely inhibited FPR1-mediated ER calcium depletion.

Figure 5A:
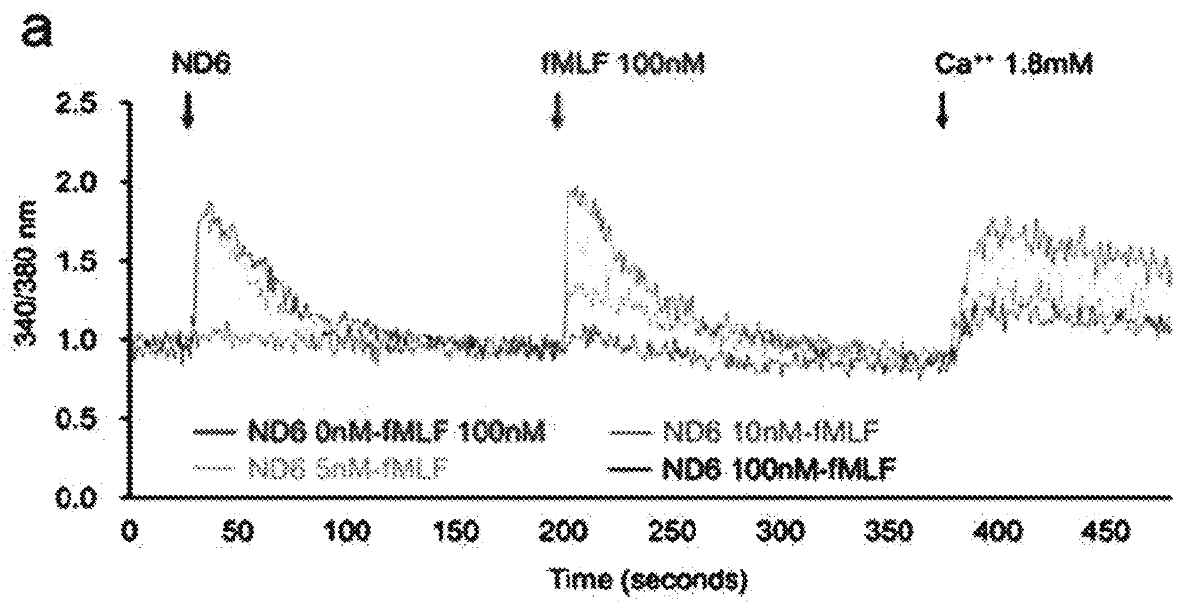
FIGS. 5*a*-5*c* relate to formyl peptide receptor 1 (FPR1)-mediated calcium mobilization and polymorphonuclear cell (PMN) chemotaxis.
Figure 5B:
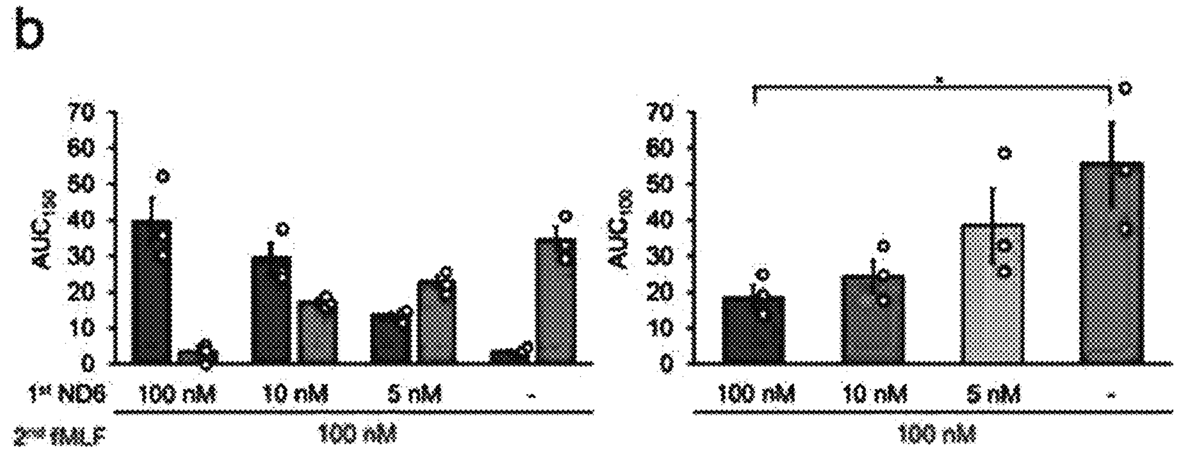
Figure 5C:
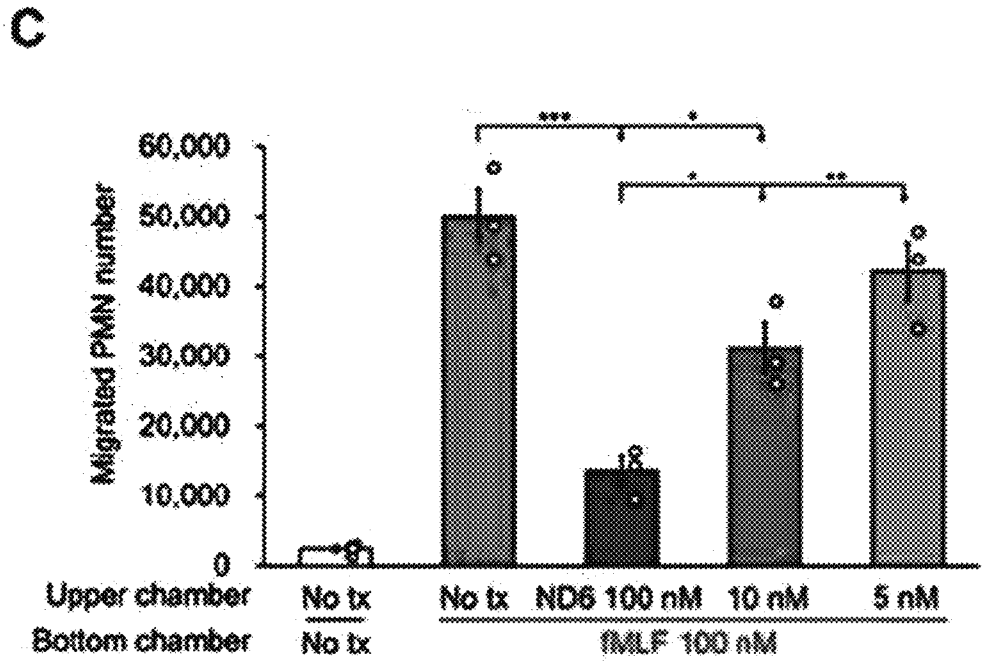
Figure 6:
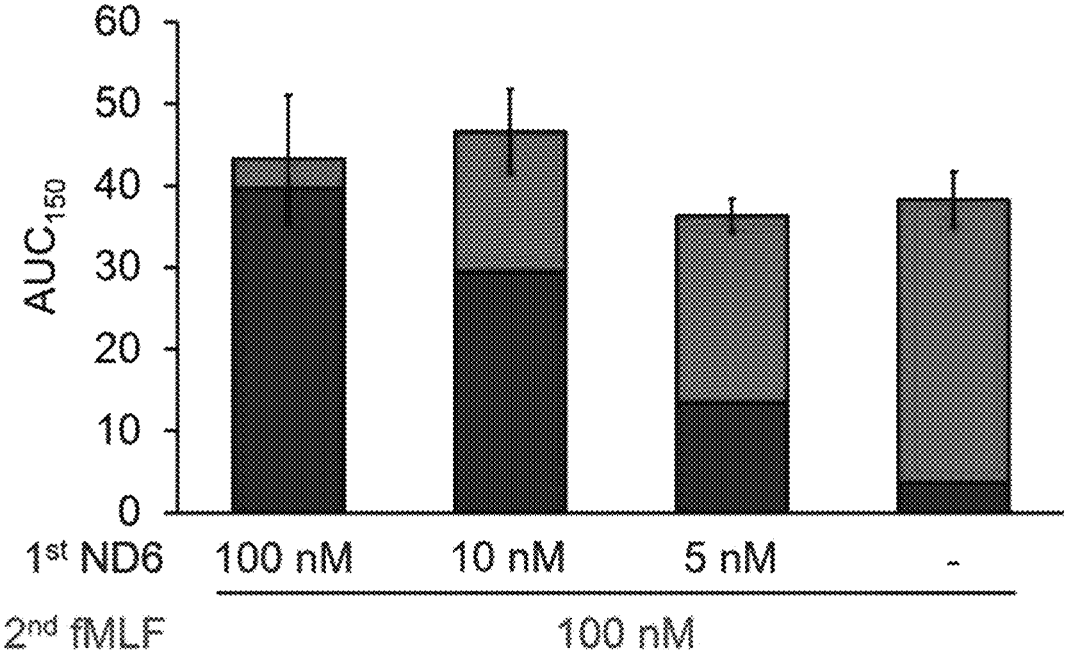
FIG. 6 relates to the total amount of FPR1-mediated ER calcium depletion. The sum of ER calcium depletion in response to 100 nM, 10 nM, 5 nM, 0 nM ND6 stimulation for 150 s ($AUC_{150}$ primary) and subsequent 100 nM fMLF stimulation ($AUC_{150}$ secondary) did not differ between experimental groups. Data are expressed as mean±standard error of three independent experiments.

ND6 treatment induced ER calcium depletion, but dose-dependently inhibited fMLF-stimulated secondary ER calcium depletion and subsequent calcium influx (FIGS. 5A and 5B). The total amount of ER calcium depletion induced by primary ND6 and secondary fMLF stimulations was similar regardless of the primary treated ND6 concentration (FIG. 6). ND6 treatment for PMNs dose-dependently inhibited PMN chemotaxis in response to 100 nM fMLF (FIG. 5C). These data indicate that after FPR1 occupancy by ND6, fMLF binds to the remainder of FPR1, leading to calcium influx and PMN chemotaxis.

Example 3

PMN Chemotaxis Rescue Following Centrifugal Removal of Circulating ND6

After exposure to 100 nM ND6 for 30 minutes, PMNs were centrifuged at 220 g for 10 minutes at 4° C., and the supernatant was discarded. The PMN pellet was resuspended in medium containing 0.1% dimethyl sulfoxide (DMSO) (ND6-DMSO group) or medium containing 100 nM ND6 (ND6-ND6 group) and incubated for 90 minutes at 37° C. on a 10-rpm rotator. Serial changes in PMN calcium mobilization at 30, 60 and 90 minutes in response to 100 nM fMLF and serial changes in PMN chemotaxis at 30 and 90 minutes in response to 100 nM fMLF were compared between the ND6-DMSO and ND6-ND6 groups. PMN chemotaxis at 30 and 90 minutes was measured as the number of PMNs migrated during 60-minute incubation between 30 and 90 minutes and 90 and 150 minutes, respectively. Additionally, in order to estimate the capacity of FPR1-mediated PMN chemotaxis, PMNs from different groups were treated with 10 μM CsH 15 minutes before incubation.

Figure 7A:
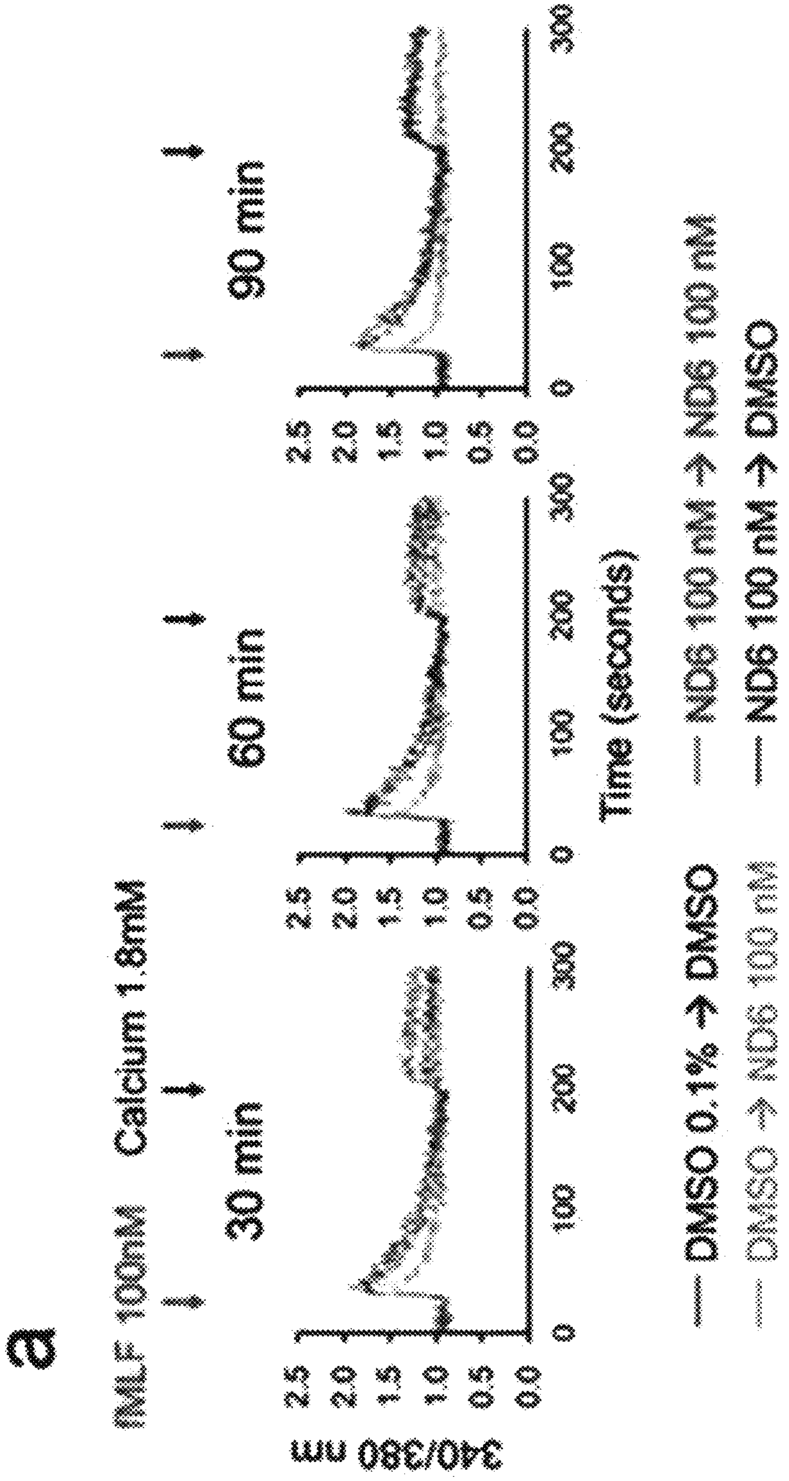
FIGS. 7*a*-7*e* relate to the structure of PMN chemotaxis after centrifugal removal of circulating ND6.
Figure 7B:
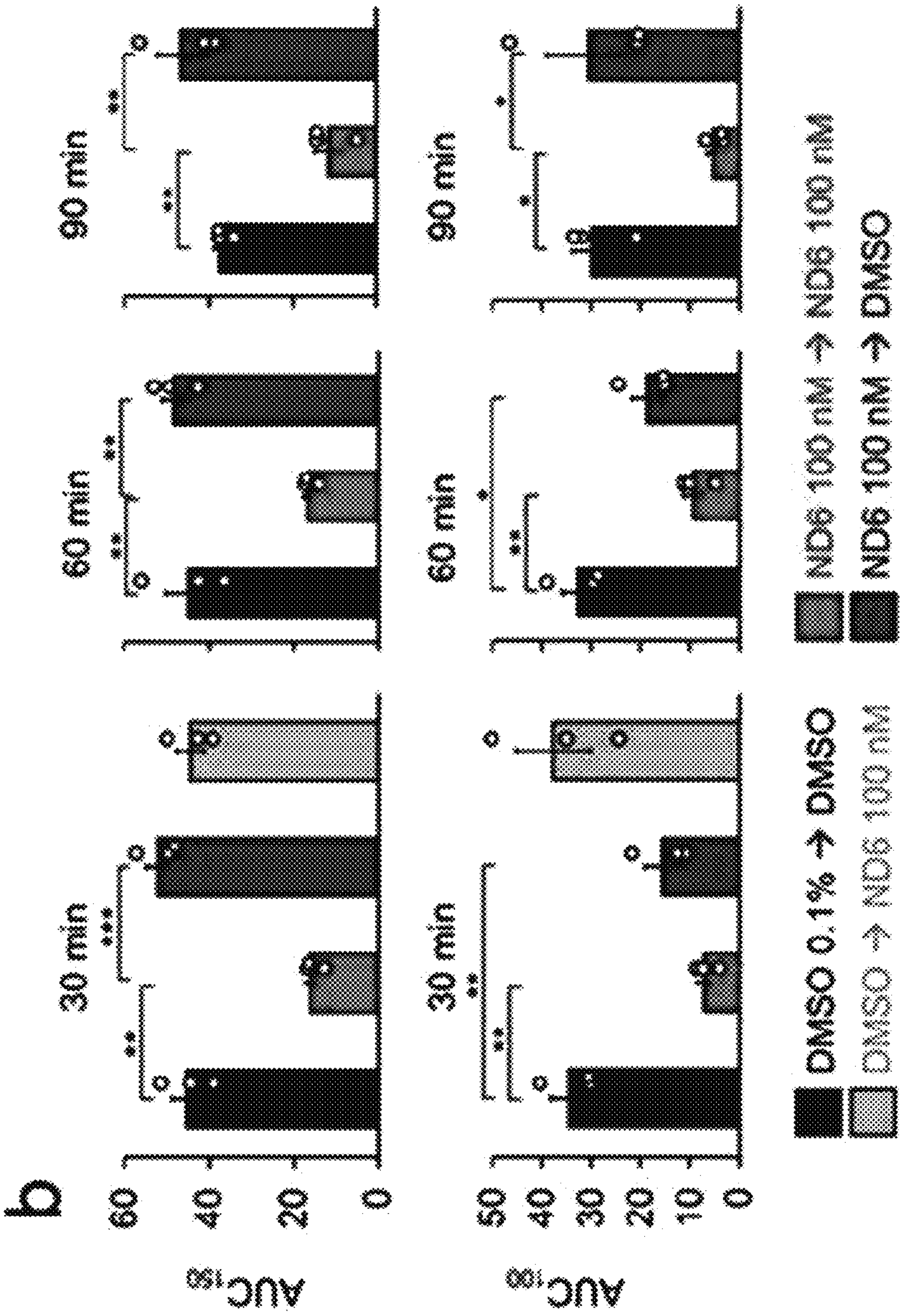
Figure 7C:
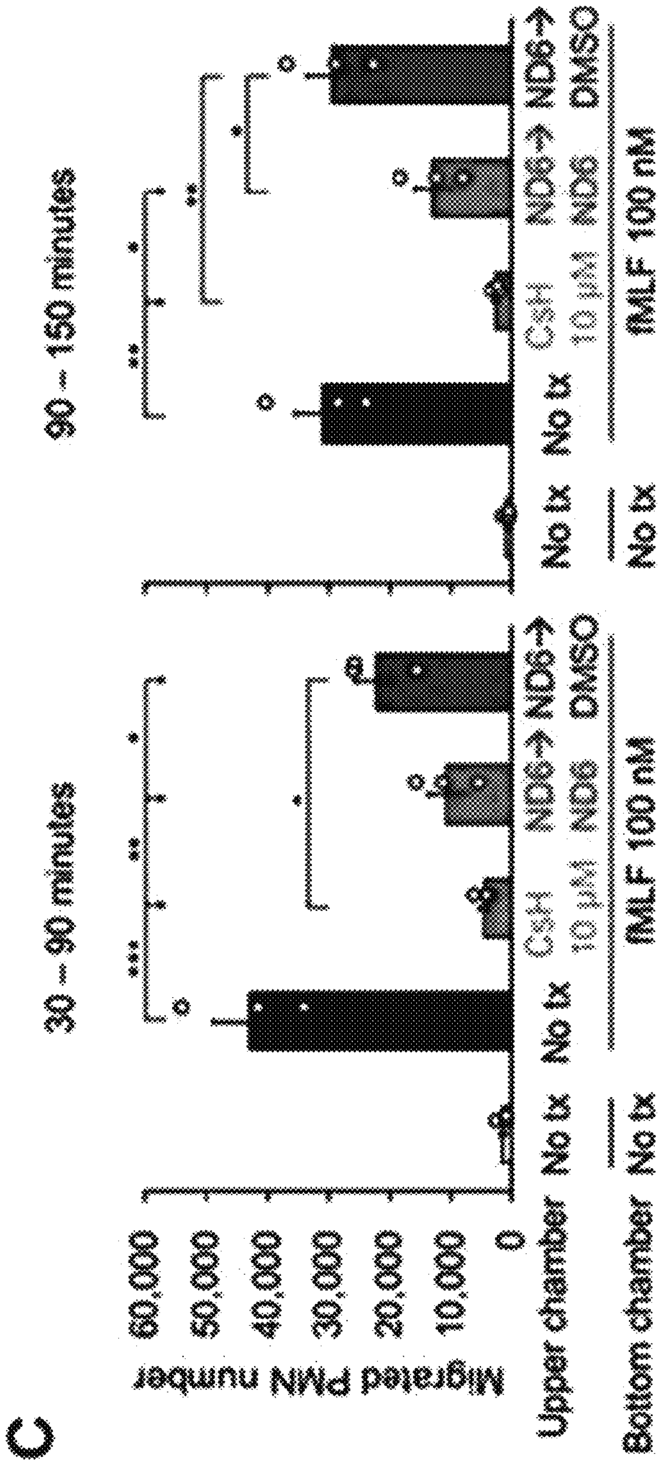
Figure 7D:
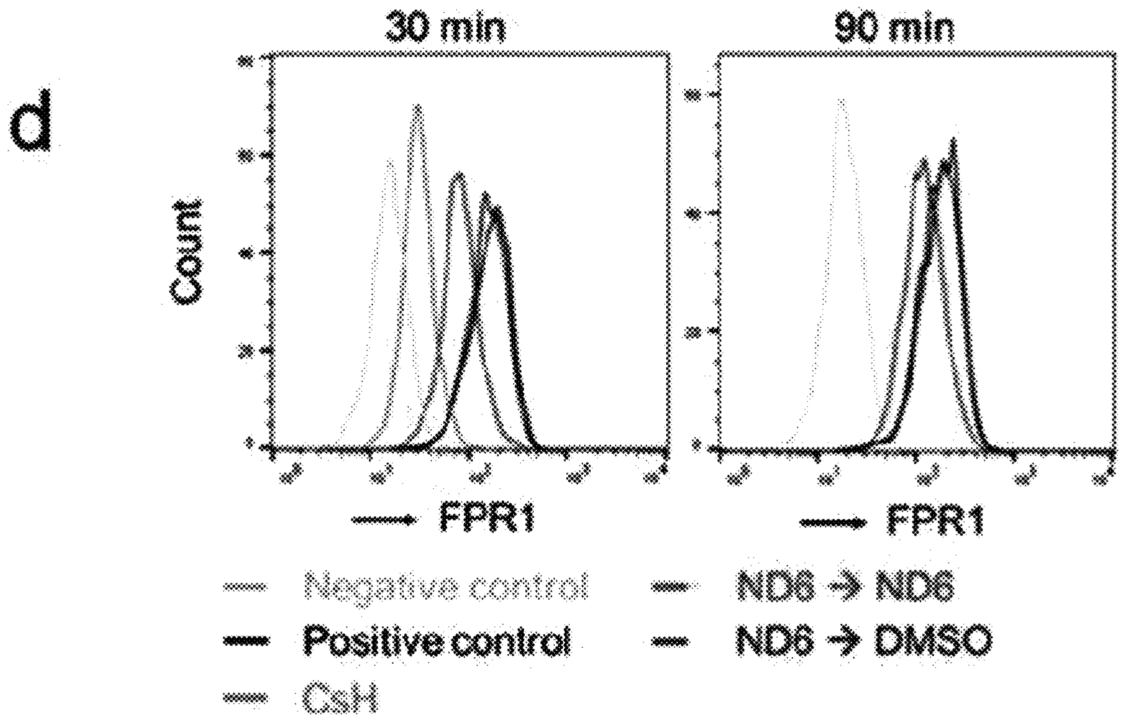
Figure 7E:
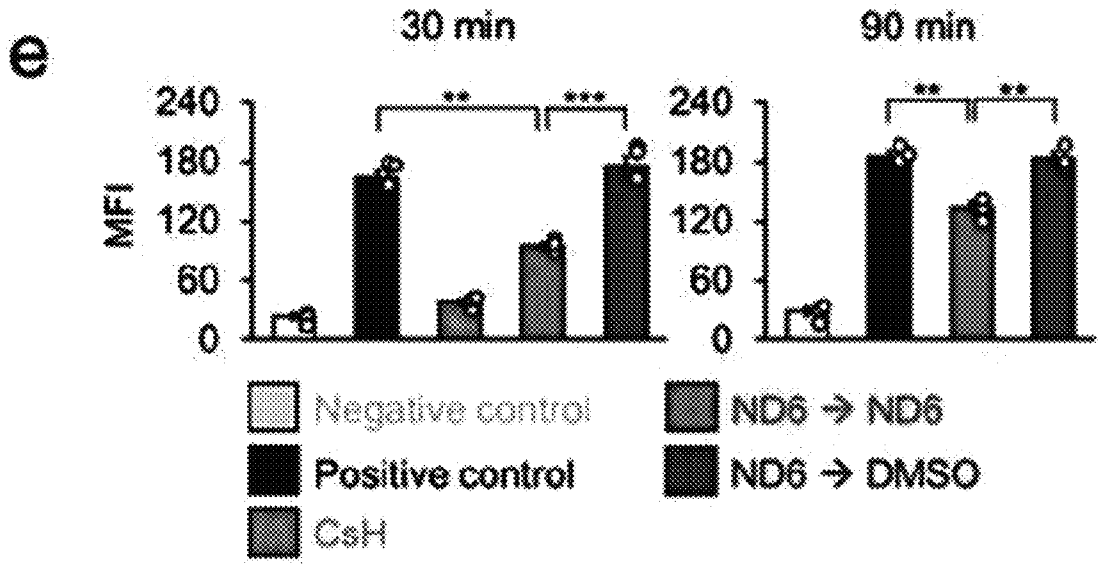

ND6 treatment inhibited ER calcium depletion, calcium influx and PMN chemotaxis in both of ND6-ND6 and ND6-DMSO groups. However, the centrifugal removal of ND6 was restored in all ND6-DMSO groups (FIGS. 7A to 7C). After 30 minutes of ND6 removal, ER calcium depletion was fully restored. In contrast to ER calcium depletion, calcium influx was still inhibited after 30 and 60 minutes, but was fully restored 90 minutes after ND6 removal (FIGS. 7A and 7B). In the ND6-DMSO group, PMN chemotaxis for fMLF was inhibited 30 minutes after ND6 removal, but fully recovered after 90 minutes (FIG. 7C). ND6 also reduced FPR1 expression in PMN membranes in both of the ND6-ND6 and ND6-DMSO groups (FIGS. 7D and 7E), but FPR1 expression in PMN membranes was fully restored 30 minutes after ND6 removal in the ND6-DMSO group (FIGS. 7D and 7E).

In contrast to short-term ND6 treatment of less than 180 seconds (FIGS. 5A and 5B), treatment with 100 nM ND6 for more than 30 minutes did not completely inhibit ER calcium depletion in response to 100 nM fMLF (FIGS. 7A and 7B). Additionally, FPR1 expression on PMN membranes in the ND6-ND6 group was found to be higher after 90 minutes of ND6 removal than after 30 minutes (FIGS. 7D and 7E). Repeated internalization of the FPR1-ND6 complex and recycling of FPR1 can reduce ND6 levels over time. In clinical situations, mtFP may be released into the circulation continuously and/or repeatedly. This situation may be different from the experimental environment in which only a single dose of ND6 was treated at the beginning of the comparative experiment.

Example 4

Correlation Between PMN Chemotaxis and Calcium Mobilization Step

Figure 8A:
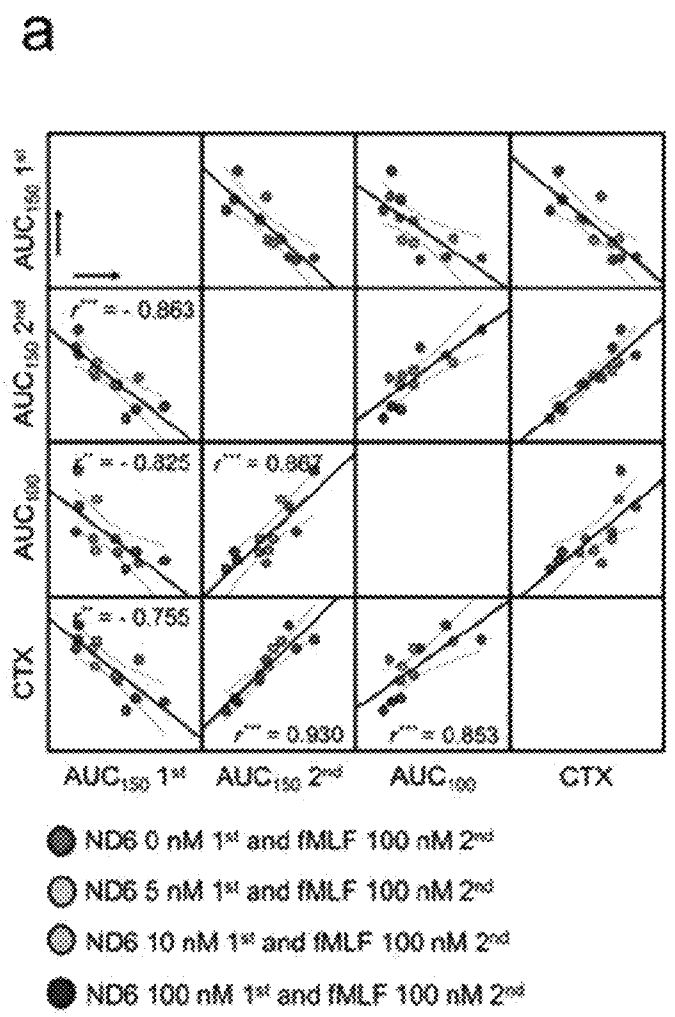
FIGS. 8*a*-8*c* relate to the correlation between PMN chemotaxis and calcium mobilization steps.

When examining the correlation between PMN chemotaxis and the calcium mobilization step in PMNs sequentially stimulated by ND6 and fMLF, PMN chemotaxis was associated with fMLF-induced ER calcium depletion ($AUC_{150}$ quadratic) (Spearman's rho=0.930) and subsequent calcium influx. ($AUC_{100}$) (rho=0.853), but inversely correlated with ND6-induced ER calcium depletion ($AUC_{150}$ $1^{st}$) (rho=−0.755) (FIG. 8A).

Figure 8B:
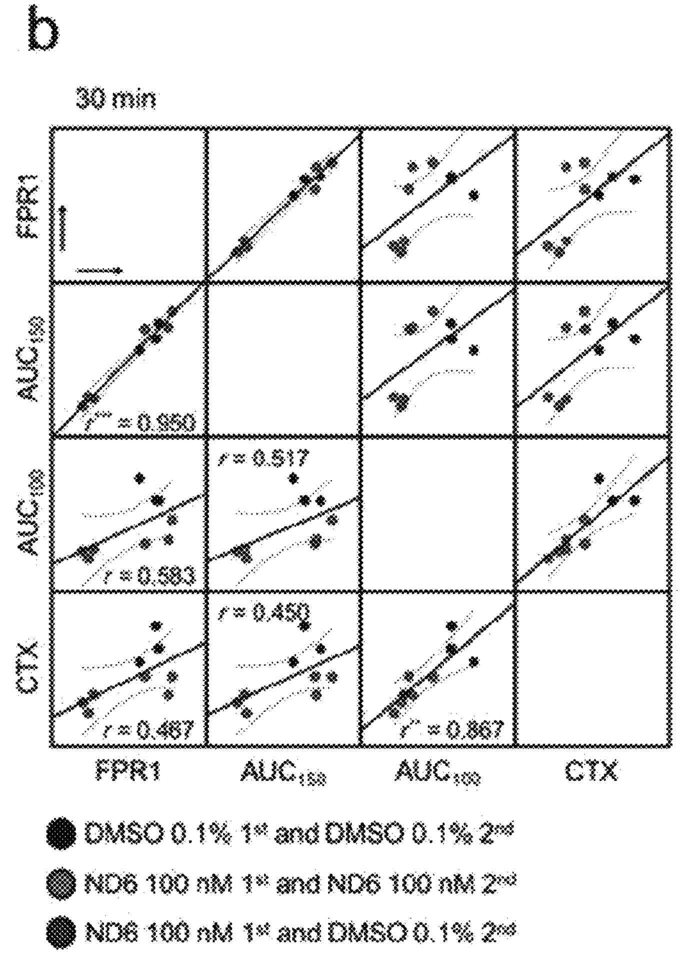
Figure 8C:
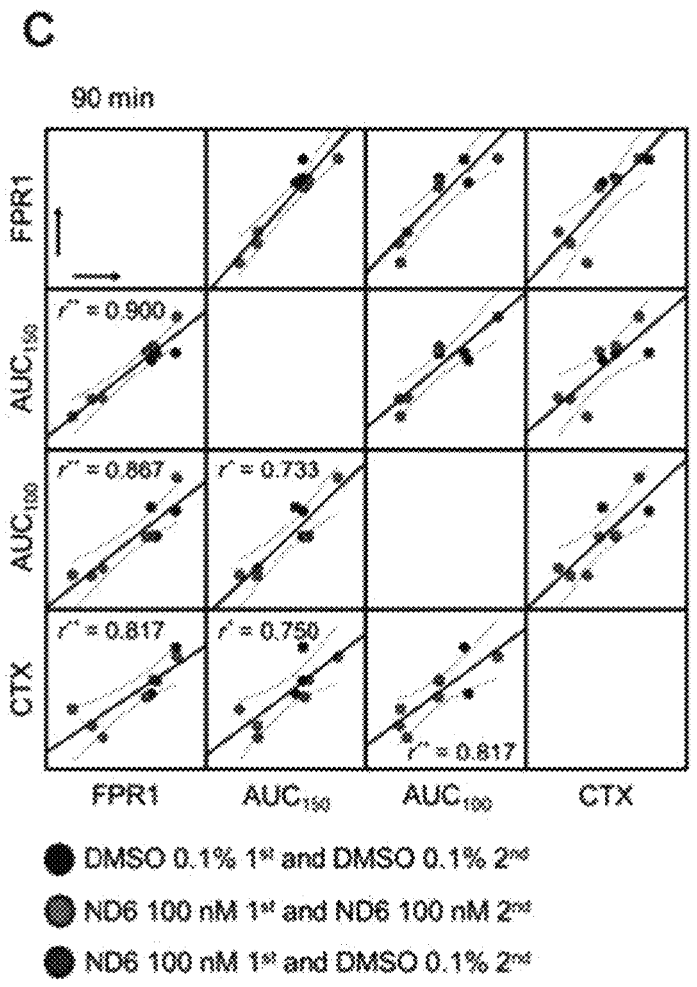

However, in ND6-exposed PMNs, after 30 minutes of centrifugal ND6 removal, FPR1 expression was significantly correlated with ER calcium depletion ($AUC_{150}$) (rho=0.950), but was not correlated with calcium influx ($AUC_{100}$) (rho=0.583) and chemotaxis (rho=0.467) (FIG. 8B). PMN chemotaxis was correlated only with calcium influx (rho=0.867). After 90 minutes of centrifugal ND6 removal, FPR1 expression, ER calcium depletion, calcium influx and chemotaxis were correlated with each other (FIG. 8C).

The above results indicate that recycled FPR1 was relocated to the PMN membrane immediately after the removal of circulating mtFP, but the recovery of calcium influx was delayed due to interfering molecules that regulate the pathway from ER calcium depletion to calcium influx. It also indicates that any therapy that eliminates circulating mtFP must be applied for at least 90 minutes to rescue PMN chemotaxis in patients recovering from septic shock.

Example 5

Preparation of Bead-Anti-mtFP Antibody Mixture

In order to achieve clinical applicability, the inventors of the present disclosure attempted to eliminate circulating mtFP with anti-mtFP antibodies, particularly those specific for potent human mtFPs, including ND6, ND3, ND4 and ND5. In order to estimate the removal ability of the anti-mtFP antibody, the difference in ND6 levels in the plasma of septic shock patients before and after treatment with the anti-ND6 antibody was measured. The characteristics of patients who donated plasma are shown in Table 1. Blood samples were collected from the patients through an arterial catheter upon admission.

TABLE 1

Characteristics of healthy volunteers and septic shock patients who donated plasma samples

| | Healthy volunteers | | | Patients with septic shock | | |
|---|---|---|---|---|---|---|
| | Person 1 | Person 2 | Person 3 | Patient 1 | Patient 2 | Patient 3 |
| Age (years) | 52 | 48 | 63 | 72 | 61 | 58 |
| Gender | Male | Female | Male | Male | Male | Female |
| Comorbidity | | | | | | |
| HT | Yes | | Yes | Yes | | |
| DM | | | | | Yes | Yes |
| Chronic liver disease | | | | | | Yes |
| Malignancy | | | | Yes | | |
| Charlson comorbidity index | | | | 10 | 5 | 7 |
| Primary infection pathogen | | | | Gram (−) | Gram (−) | Gram (+) |
| Bacteremia | | | | Yes | Yes | Yes |
| Primary infection site | | | | Respiratory | Hepatobiliary | Gastrointestinal |
| Lactate level (mmol/L) | | | | 13.7 | 8.4 | 10.2 |
| SOFA score at admission | | | | 16 | 10 | 13 |

TABLE 1-continued

| Characteristics of healthy volunteers and septic shock patients who donated plasma samples | | | | | | |
|---|---|---|---|---|---|---|
| | Healthy volunteers | | | | | |
| | Person | Person | Person | Patients with septic shock | | |
| | 1 | 2 | 3 | Patient 1 | Patient 2 | Patient 3 |
| Respiratory | | | | 4 | 1 | 3 |
| Cardiovascular | | | | 4 | 3 | 4 |
| Liver | | | | 1 | 3 | 2 |
| Renal | | | | 2 | 0 | 1 |
| Coagulation | | | | 2 | 3 | 2 |
| Neurologic | | | | 3 | 0 | 1 |
| Management | | | | | | |
| Time to 1st antibiotics (hours) | | | | 0.5 | 0.7 | 0.9 |
| MV duration | | | | 53 | 0 | 17 |
| Renal replacement therapy | | | | Yes | | Yes |
| Hydrocortisone | | | | Yes | | Yes |
| Source control | | | | | Endoscopic | |
| Blood sample (hospital day) | | | | 1 | 2 | 1 |
| Clinical outcome | | | | | | |
| 90-day survival | | | | Death | Survival | Survival |
| Survival days till 90 days (days) | | | | 53 | 90 | 90 |

HT = hypertension; DM = diabetes mellitus; SOFA = Sequential Organ Failure Assessment; MV = mechanical ventilation.

Figure 9:
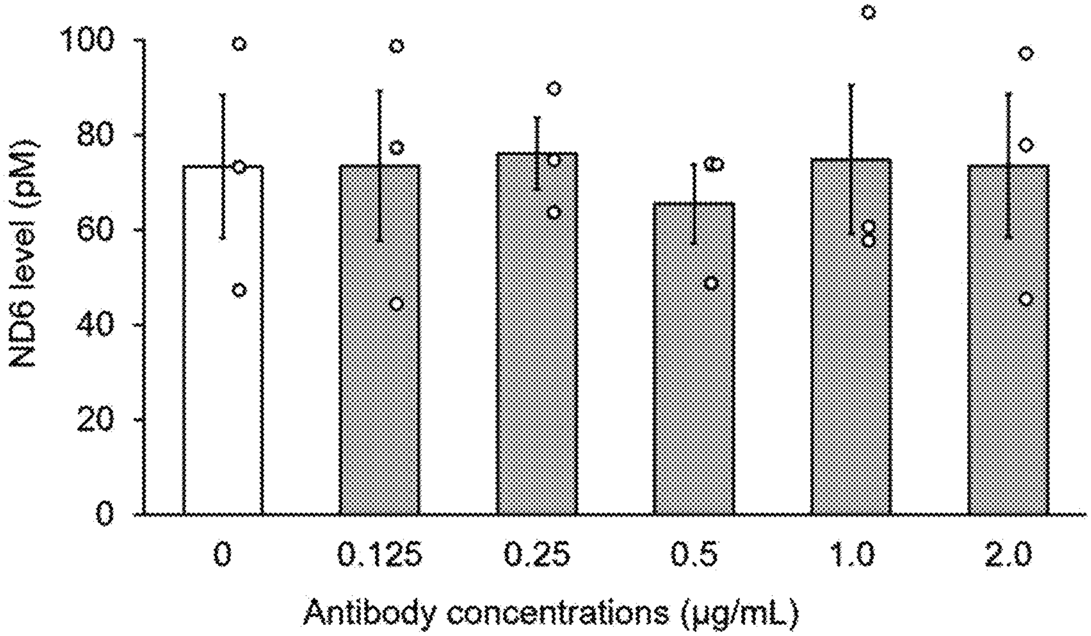
FIG. 9 relates to changes in plasma ND6 levels following direct anti-ND6 antibody treatment. Direct anti-ND6 antibody treatment of plasma did not change ND6 levels in plasma obtained from patients with septic shock. Data are expressed as mean±standard error of three independent experiments.

Direct anti-ND6 antibody treatment of plasma did not affect plasma ND6 levels (FIG. 9). Therefore, the inventors of the present disclosure prepared a beat-anti-ND6 antibody complex by binding the protein A/sepharose (80 μL) to 0.0.25 μg/mL, 0.5 μg/mL, 1.0 μg/mL, 2.0 μg/mL, 4.0 μg/mL or 8.0 μg/mL of the anti-ND6 antibody for 4 hours on a 10-rpm rotator at 4° C. After 2 hours of incubation with plasma on a 10-rpm rotator at 37° C., the bead-anti-ND6 complex was removed from plasma by centrifugation at 20,000 g for 10 minutes at 4° C. In order to investigate the non-specific binding of mtFP to beads, ND6 levels were also compared between plasma treated with only beads and plasma without treatment. The bead-anti-ND6 complex removed ND6 from plasma in a dose-dependent manner while minimizing the non-specific binding of ND6 to the beads (FIGS. 11A and 11B). An anti-ND6 antibody concentration of 4.0 μg/mL reduced plasma ND6 levels between 100 pM and 150 pM (FIG. 11B). In previous studies, the inventors of the present disclosure selected 5.0 μg/mL as the optimal antibody concentration for clinical application, because the difference in plasma ND6 levels between septic shock patients who developed secondary infection and patients negative secondary infection patients was 87 pM.

Based on these results, the protein A/sepharose (320 μL) was combined with specific antibodies for 4 mtFPs: ND6, ND3, ND4 and ND5 in order to remove potent mtFPs from the plasma of septic shock patients at once (bead-anti-mtFP mixture). 2.5 μg of each antibody was administered, and the final concentration was adjusted to 5.0 μg/mL in 500 μL plasma. After 2 hours of incubation with plasma on a 10-rpm rotator at 37° C., the bead-anti-mtFP mixture reduced the plasma levels of ND6, ND3, ND4 and ND5 to 139 pM, 112 pM, 104 pM, and 135 pM, respectively (FIGS. 12A and 12B) (Table 2). However, the bead-anti-mtFP mixture did not significantly remove other cytokines such as tumor necrosis factor (TNF)-α, interleukin (IL)-1β, IL-6 and IL-10 and chemokines such as growth regulatory oncogene (GRO)-α, IL-8 and leukotriene B4 (LTB4) (FIG. 12C) (Table 2).

TABLE 2

Changes in plasma molecular levels in septic shock patients upon ICU admission after treating bead-anti-mtFP mixture
Mean ± standard error (SE)

| | | Bead-anti-mtFP cocktail treatment | |
|---|---|---|---|
| | Healthy volunteers N = 3 | Pre N = 3 | Post N = 3 |
| mtFPs | | | |
| ND6 (pM) | 23.50 ± 1.41 | 160.36 ± 63.96 | 20.89 ± 0.99 |
| ND3 (pM) | 99.28 ± 12.32 | 278.10 ± 22.04 | 165.61 ± 12.32 |
| ND4 (pM) | 26.50 ± 5.42 | 136.70 ± 26.83 | 32.50 ± 5.81 |
| ND5 (pM) | 34.83 ± 12.95 | 235.25 ± 83.28 | 99.90 ± 46.88 |

TABLE 2-continued

Changes in plasma molecular levels in septic shock patients upon ICU admission after treating bead-anti-mtFP mixture
Mean ± standard error (SE)

| | Healthy volunteers N = 3 | Bead-anti-mtFP cocktail treatment Pre N = 3 | Bead-anti-mtFP cocktail treatment Post N = 3 |
|---|---|---|---|
| Cytokines | | | |
| TNF-α (pg/mL) | 24.24 ± 2.69 | 831.44 ± 342.17 | 762.09 ± 299.46 |
| IL-1β (pg/mL) | 6.78 ± 2.24 | 111.35 ± 28.38 | 100.35 ± 24.50 |
| IL-6 (pg/mL) | 95.18 ± 0.73 | 13739.76 ± 5304.22 | 12767.96 ± 5024.85 |
| IL-10 (pg/mL) | 20.09 ± 3.54 | 5024.05 ± 882.42 | 4830.23 ± 884.33 |
| Chemokines | | | |
| GRO-α (pg/mL) | 101.29 ± 4.75 | 7975.69 ± 3509.01 | 7434.75 ± 3099.85 |
| IL-8 (pg/mL) | 79.97 ± 2.84 | 3394.73.45 ± 1441.02 | 3207.63 ± 1345.04 |
| LTB4 (pg/mL) | 20.10 ± 2.54 | 87.86 ± 16.83 | 81.25 ± 16.37 |

ICU = intensive care unit; ND = nicotinamide adenine dinucleotide dehydrogenase subunit; pM = picomolar; TNF-α = tumor necrosis factor-α; IL-1β = interleukin-1β; IL-6 = interleukin 6; IL-10 = interleukin 10; GRO-α = growth-regulated oncogene-α; IL-8 = interleukin 8; LTB4 = leukotriene B4.

Figure 12A:
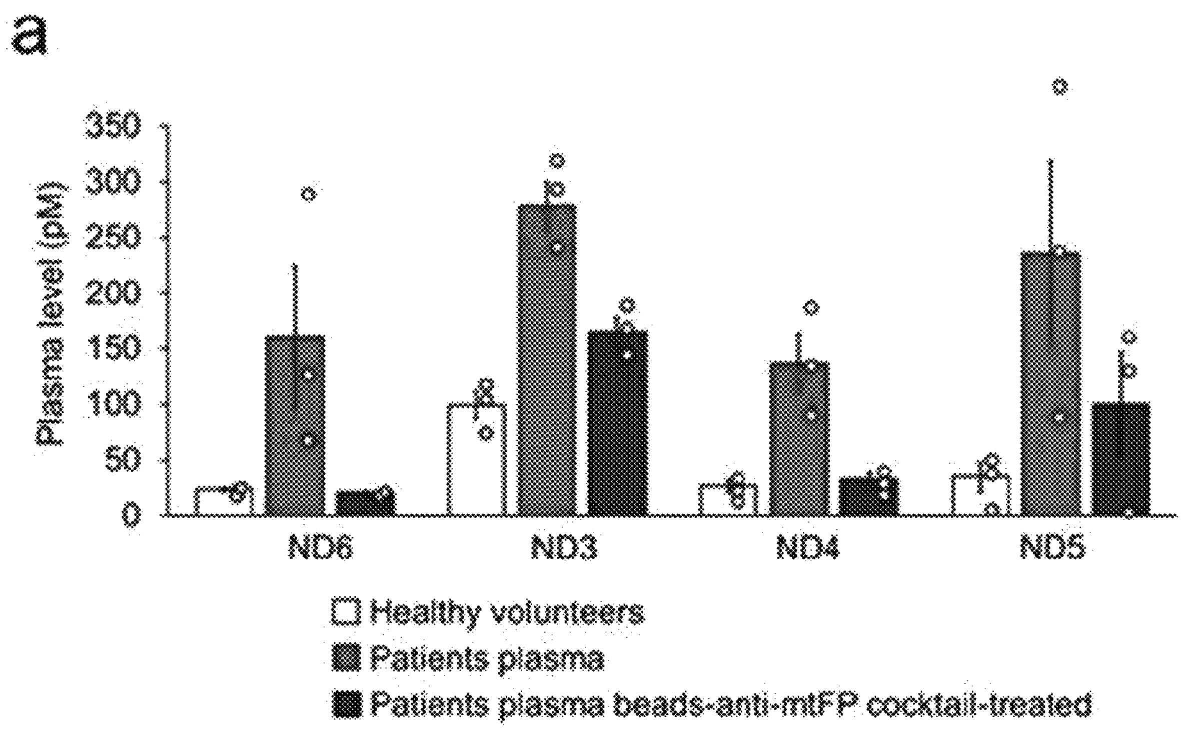
FIGS. 12*a*-12*d* relate to the therapeutic effect of a beads-anti-mtFP cocktail.
Figure 12B:
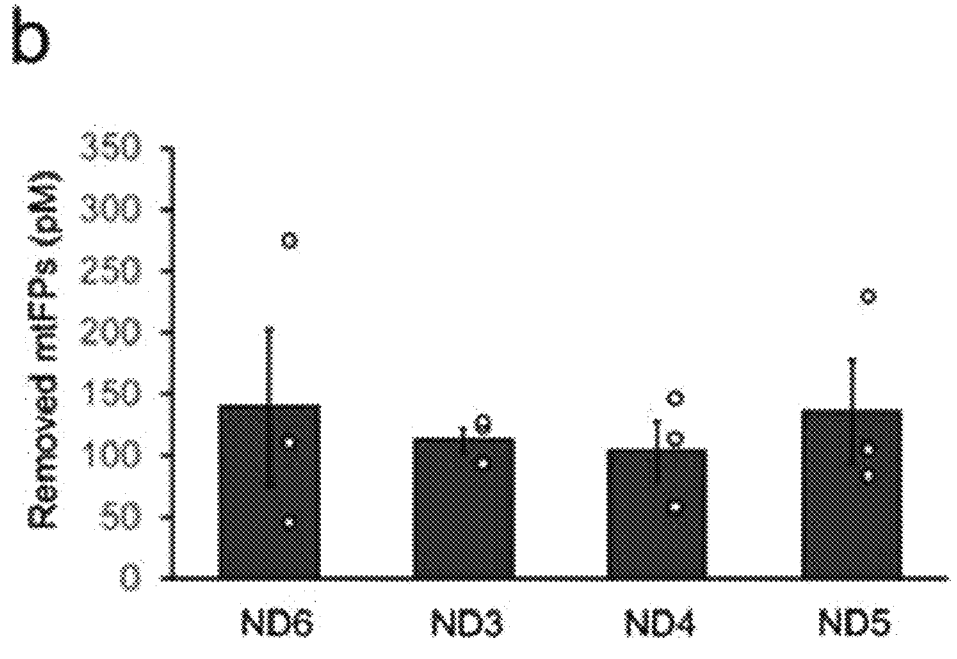
Figure 12C:
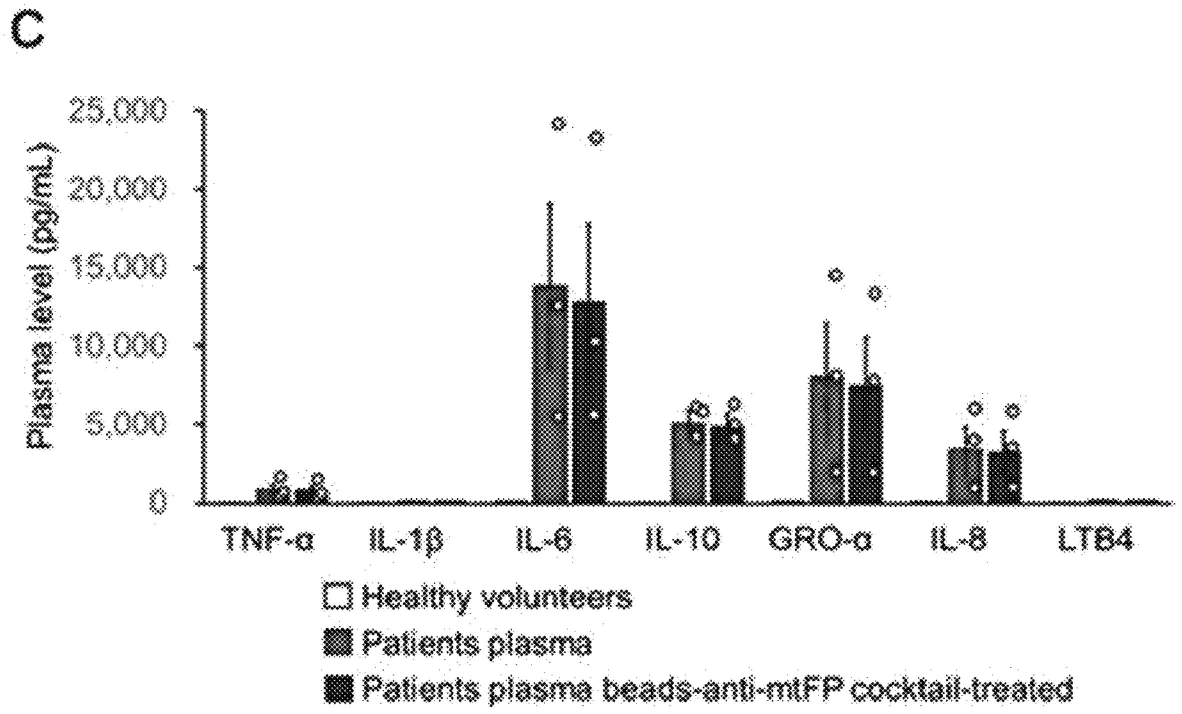
Figure 12D:
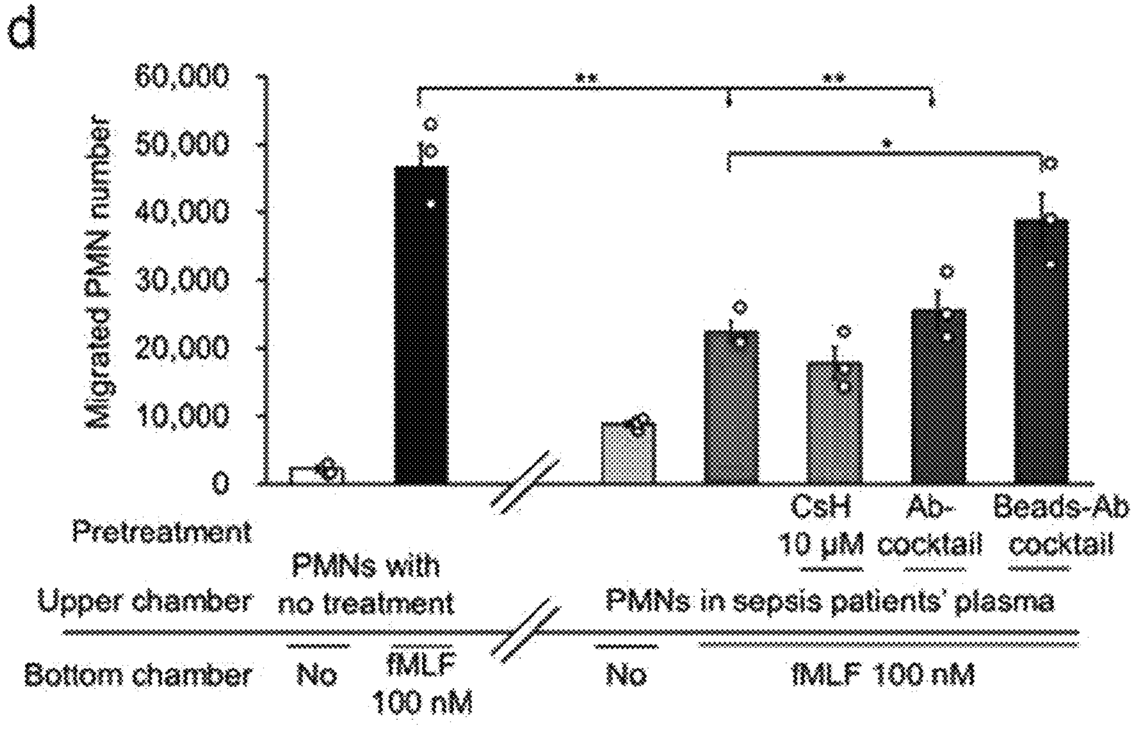

The inventors of the present disclosure investigated the chemotactic restoration effect of the anti-mtFP cocktail on PMNs by exposing PMNs from healthy volunteers to the plasma of septic shock patients treated with the anti-mtFP cocktail and then comparing PMN chemotaxis with plasma that had not received the anti-mtFP cocktail treatment. After exposing PMNs from healthy volunteers to untreated plasma from septic shock patients for 30 minutes, PMNs were centrifuged at 220 g for 10 minutes at 4° C., and the supernatant was discarded. PMN pellets were resuspended in untreated plasma, direct anti-mtFP antibody treated plasma or the bead anti-mtFP mixture treated plasma and incubated for 90 minutes on a 10-rpm rotator at 37° C. Next, PMN chemotaxis for 100 nM fMLF was measured. Untreated plasma from septic shock patients inhibited healthy volunteer PMN chemotaxis in response to fMLF. Direct anti-mtFP antibody treatment could not restore PMN chemotaxis, but the bead-anti-mtFP mixture treatment significantly restored PMN chemotaxis (FIG. 12D). When additional 10 μM CsH was added to PMNs at the start of incubation, the chemotaxis of CsH-treated-PMNs exposed to untreated plasma was not significantly different from the chemotaxis of CsH-free PMNs exposed to untreated plasma (FIG. 12D). These results indicate that the rescue of PMN chemotaxis through the bead-anti-mtFP mixture treatment is primarily mediated by inhibiting recycled FPR1-occupancy by circulating mtFP.

Example 6

Rescue of PMN Chemotaxis in Septic Shock Patients with Secondary Infection by Bead-Anti-mtFP Combination Treatment.

The inventors of the present disclosure studied whether the bead-anti-mtFP mixture removes circulating mtFP and restores PMN chemotaxis in septic shock patients with secondary infection to the level of patients negative for secondary infection. The characteristics of patients who donated PMN and plasma are shown in Table 3. Blood samples were collected through an arterial catheter from patients who were recognized to have developed a secondary infection between 10 and 14 days after admission to the ICU (n=3). Secondary infections, including ventilator-associated pneumonia (VAP), central line-associated blood stream infection (CLABSI) and catheter-associated urinary tract infection (CAUTI), were defined according to the 2019 National Healthcare Safety Network (NHSN) Patient Safety Components Manual published by the Centers for Disease Control and Prevention. In addition, blood samples were collected from septic shock patients who did not develop secondary infections between 10 and 14 days after hospitalization (n=3).

TABLE 3

Characteristics of septic shock patients who developed secondary infection in hospital who donated PMNs and plasma and septic shock patients who did not develop secondary infection

| | $2^{nd}$ infection (−) | | | $2^{nd}$ infection (+) | | |
|---|---|---|---|---|---|---|
| | Patient 1 | Patient 2 | Patient 3 | Patient 1 | Patient 2 | Patient 3 |
| Age (years) | 71 | 81 | 64 | 66 | 73 | 77 |
| Gender | Male | Male | Female | Female | Male | Male |
| Comorbidity | | | | | | |
| HT | | Yes | Yes | Yes | | |
| DM | Yes | | | Yes | | Yes |
| Chronic liver disease | | | | | Yes | |
| Malignancy | Yes | | | | Yes | |
| Charlson comorbidity index | 11 | 5 | 6 | 7 | 11 | 10 |

TABLE 3-continued

Characteristics of septic shock patients who developed secondary infection in hospital who donated PMNs and plasma and septic shock patients who did not develop secondary infection

| | $2^{nd}$ infection (−) | | | $2^{nd}$ infection (+) | | |
|---|---|---|---|---|---|---|
| | Patient 1 | Patient 2 | Patient 3 | Patient 1 | Patient 2 | Patient 3 |
| Primary infection pathogen | Gram (−) | Gram (+) | Gram (−) | Gram (+) | Gram (−) | Gram (−) |
| Bacteremia | Yes | Yes | | | Yes | Yes |
| Primary infection site | Hepatobiliary | Respiratory | Gastrointestinal | Respiratory | Gastrointestinal | Respiratory |
| Lactate level (mmol/L) | 6.8 | 10.4 | 9.1 | 5.9 | 12.6 | 9.5 |
| SOFA score at admission | 10 | 14 | 12 | 11 | 17 | 14 |
| Respiratory | 0 | 3 | 2 | 4 | 2 | 4 |
| Cardiovascular | 3 | 4 | 4 | 3 | 4 | 4 |
| Liver | 4 | 1 | 3 | 1 | 3 | 2 |
| Renal | 1 | 2 | 0 | 1 | 3 | 0 |
| Coagulation | 2 | 1 | 2 | 0 | 3 | 2 |
| Neurologic | 0 | 2 | 1 | 2 | 2 | 2 |
| Management | | | | | | |
| Time to $1^{st}$ antibiotics (hours) | 0.7 | 1.0 | 0.9 | 0.8 | 0.4 | 0.8 |
| MV duration | 0 | 21 | 16 | 14 | 29 | 53 |
| Renal replacement therapy | | Yes | | Yes | Yes | |
| Hydrocortisone | | Yes | Yes | Yes | Yes | Yes |
| Source control | Radiologic | | | | | |
| Secondary infection | | | | | | |
| Secondary infection site | | | | VAP | CLABSI | VAP |
| Isolated pathogen | | | | *Acinetobacter baumanii* | *Enterococcus faecium* | *Pseudomonas aeruginosa* |
| Detection (hospital day) | | | | 10 | 13 | 11 |
| Blood sample (hospital day) | 14 | 10 | 13 | 10 | 14 | 12 |
| SOFA score at secondary infection | 7 | 12 | 6 | 9 | 14 | 13 |
| Respiratory | 1 | 2 | 1 | 4 | 1 | 3 |
| Cardiovascular | 2 | 2 | 1 | 3 | 2 | 3 |
| Liver | 2 | 1 | 2 | 0 | 4 | 1 |
| Renal | 1 | 2 | 0 | 1 | 2 | 2 |
| Coagulation | 1 | 2 | 2 | 0 | 3 | 2 |
| Neurologic | 0 | 3 | 0 | 1 | 2 | 2 |
| Clinical outcome | | | | | | |
| 90-day survival | Survival | Death | Survival | Survival | Death | Death |
| Survival days till 90 days (days) | 90 | 78 | 90 | 90 | 29 | 53 |

$2^{nd}$ infection (−) = secondary infection-negative patients; $2^{nd}$ infection (+) = patients with septic shock who developed secondary infection; HT = hypertension; DM = diabetes mellitus; SOFA = Sequential Organ Failure Assessment; MV = mechanical ventilation; VAP = ventilator-associated pneumonia; CLABSI = central line-associated blood stream infection.

Cell-free plasma was prepared by separating plasma from blood samples collected from septic shock patients. Next, half of the cell-free plasma was incubated with the bead-anti-mtFP mixture for 2 hours at 37° C. on a 10-rpm rotator, and the other half of the cell-free plasma was incubated without the bead-anti-mtFP mixture. Plasma from patients negative for secondary infection was not treated with the bead anti-mtFP mixture. During the plasma incubation period, PMNs from patients were isolated and incubated in untreated plasma for 30 minutes on a 10-rpm rotator at 37° C. After centrifugation at 220 g for 10 minutes at 4° C., the supernatant was discarded. PMN pellets were resuspended in untreated plasma or bead-anti-mtFP mixture-treated plasma and incubated for 90 minutes on a 10-rpm rotator at 37° C. Next, changes in PMN chemotaxis for fMLF were compared.

Figure 13A:
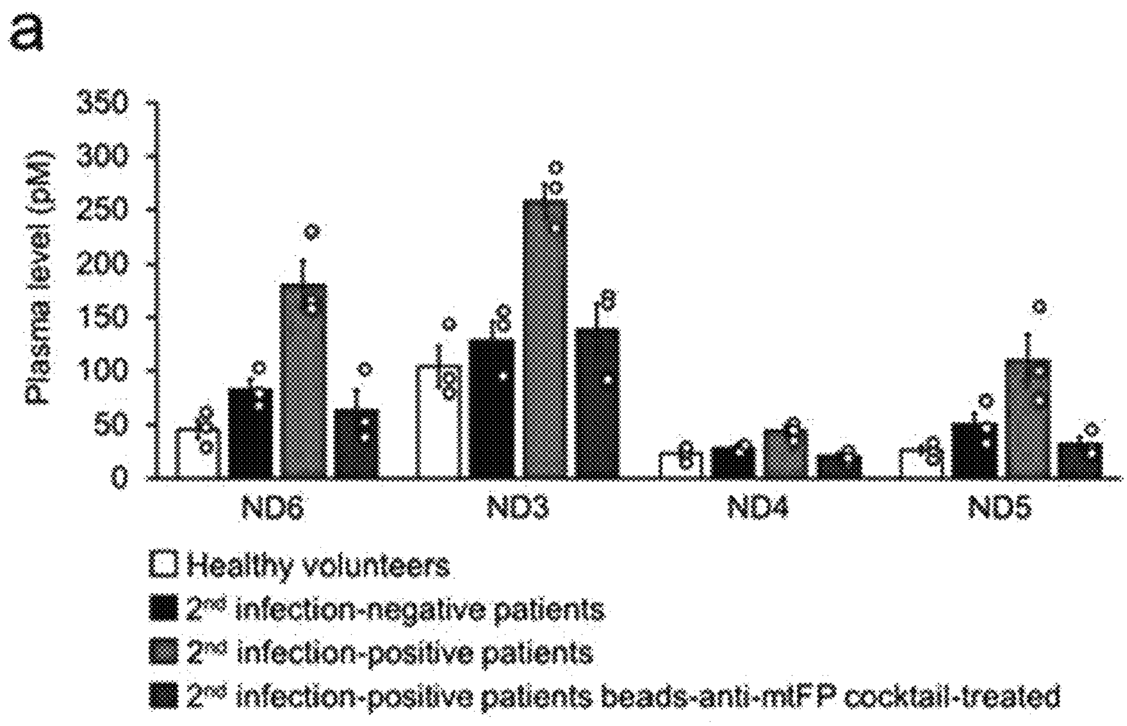
FIG. 13*a* relates to mtFP levels in plasma from septic shock patients who developed secondary infections and patients negative for secondary infections before and after treatment with the bead-anti-mtFP mixture.
Figure 13B:
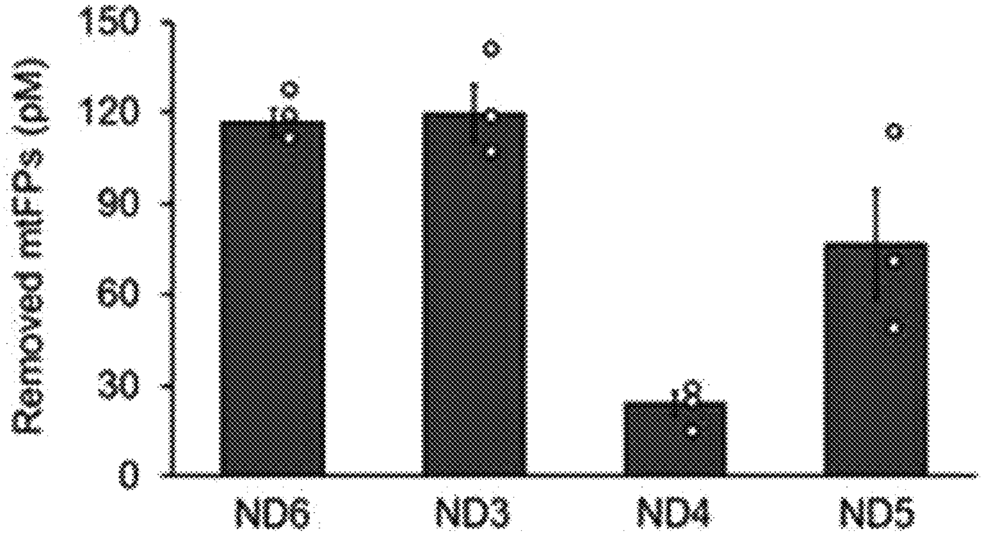
FIG. 13*b* relates to the amount of mtFP removed by the bead-anti-mtFP mixture, and FIG. 13*c* relates to plasma cytokine and chemokine levels before and after the bead-anti-mtFP mixture treatment. In plasma obtained from septic shock patients with secondary infection, bead-anti-mtFP successfully removed circulating mtFP, but did not significantly remove cytokines and chemokines.
Figure 13C:
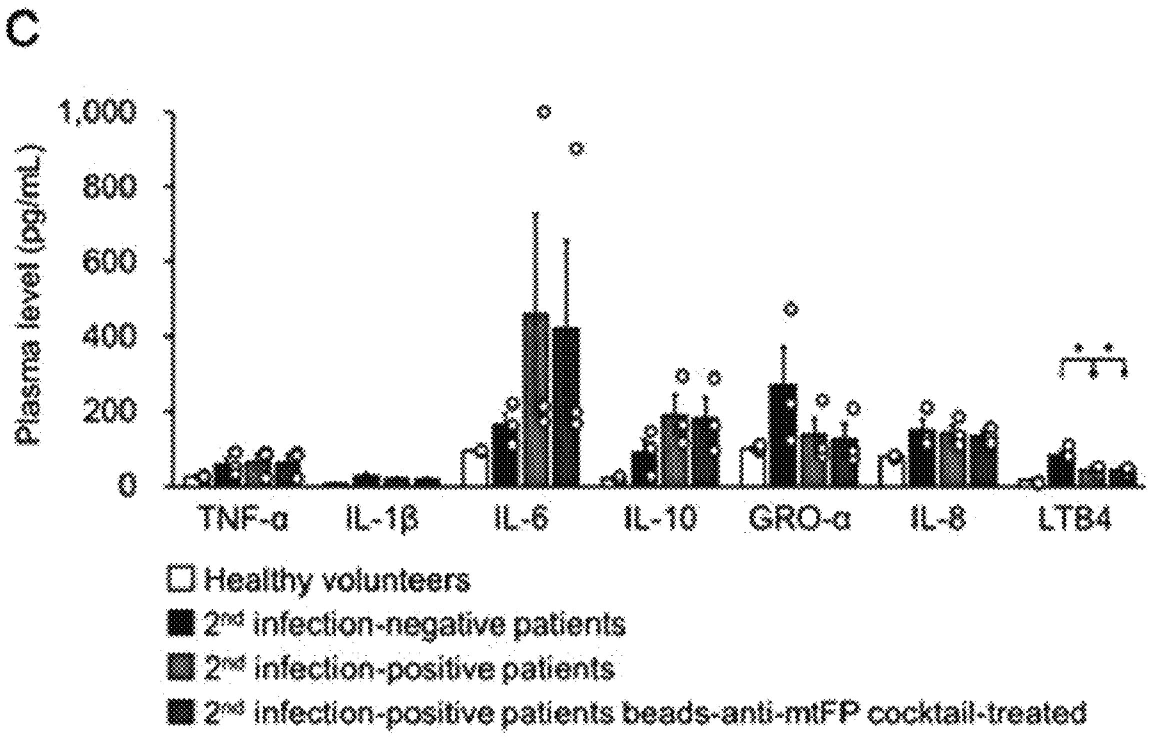
FIGS. 13***a*-13*d* relate to the structure of PMN chemotaxis in septic shock patients who developed secondary infection through the bead-anti-mtFP mixture treatment.
FIG. 13*d* relates to the structure of PMN chemotaxis in septic shock patients with secondary infection. PMNs isolated from septic shock patients with secondary infection were exposed to their own plasma for 30 minutes. Next, PMNs were resuspended in plasma not treated with the bead-anti-mtFP mixture or plasma treated with the bead-anti-mtFP mixture and incubated for 90 minutes. Plasma from patients negative for secondary infection was not treated with bead-anti-mtFP. PMNs isolated from patients negative for secondary infection were also incubated with their own plasma, and PMN chemotaxis was measured. When exposed to plasma, the chemotaxis of PMNs isolated from septic shock patients who developed secondary infections was significantly lower than the chemotaxis of PMNs isolated from patients negative for secondary infections.
Figure 13D:
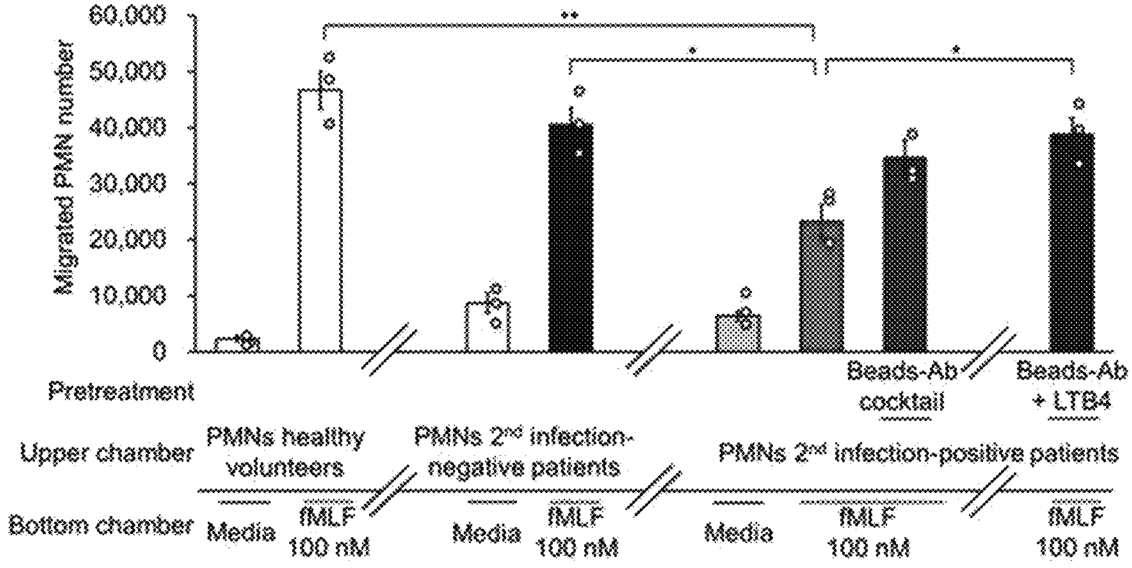

In the plasma of septic shock patients who developed secondary infections, the bead anti-mtFP mixture treatment reduced the plasma levels of ND6, ND3, ND4 and ND5 by 139 pM, 112 pM, 104 pM, and 135 pM, respectively (FIGS. 13A and 13B) (Table 4), but did not significantly remove other cytokines and chemokines (FIG. 13C) (Table 4). When exposed to their own plasma, the chemotaxis of PMNs obtained from septic shock patients who developed secondary infections was significantly lower than the chemotaxis of PMNs obtained from patients negative for secondary infections (FIG. 13D). However, significant differences in chemotaxis were lost in PMNs obtained from septic shock patients who developed secondary infections exposed to their own plasma treated with the bead-anti-mtFP mixture (FIG. 13D).

TABLE 4

Changes in plasma molecular levels before and after bead-anti-mtFP mixture treatment during secondary infection in patients recovering from septic shock

| | | Mean ± standard error (SE) 2nd infection (+) | |
|---|---|---|---|
| | 2nd infection (−) N = 3 | No treatment N = 3 | Bead-anti-mtFPs N = 3 |
| mtFPs | | | |
| ND6 (pM) | 82.01 ± 9.80 | 180.47 ± 22.04 | 63.86 ± 18.42 |
| ND3 (pM) | 128.38 ± 18.00 | 257.99 ± 16.11 | 138.52 ± 24.42 |
| ND4 (pM) | 28.30 ± 1.22 | 44.89 ± 4.78 | 20.94 ± 3.13 |
| ND5 (pM) | 50.40 ± 11.18 | 108.93 ± 24.97 | 32.30 ± 6.73 |
| Cytokines | | | |
| TNF-α (pg/mL) | 57.85 ± 17.49 | 65.28 ± 21.91 | 63.92 ± 21.69 |
| IL-1β (pg/mL) | 26.17 ± 7.99 | 18.41 ± 4.31 | 17.06 ± 3.18 |
| IL-6 (pg/mL) | 164.48 ± 32.00 | 460.13 ± 267.66 | 421.05 ± 238.59 |
| IL-10 (pg/mL) | 91.23 ± 34.50 | 190.40 ± 53.36 | 181.62 ± 55.95 |
| Chemokines | | | |
| GRO-α (pg/mL) | 271.06 ± 104.09 | 136.39 ± 46.37 | 125.28 ± 41.90 |
| IL-8 (pg/mL) | 149.76 ± 30.14 | 142.99 ± 21.95 | 134.04 ± 12.11 |
| LTB4 (pg/mL) | 84.26 ± 8.99 | 42.82* ± 10.61 | 42.08* ± 8.21 |

2nd infection (−) = secondary infection-negative patients; 2nd infection (+) = patients with septic shock who developed secondary infection; Bead-anti-mtFPs = bead-anti-mtFP cocktail treated; ND = nicotinamide adenine dinucleotide dehydrogenase subunit; pM = picomolar; TNF-α = tumor necrosis factor-α; IL-1β = interleukin-1β; IL-6 = interleukin 6; IL-10 = interleukin 10; GRO-α = growth-regulated oncogene-α; IL-8 = interleukin 8; LTB4 = leukotriene B4.

*$P < 0.05$ versus 2nd infection (−).

In contrast to PMNs obtained from healthy volunteers, chemotaxis was shown to be restored in PMNs obtained from septic shock patients who developed secondary infections exposed to bead-anti-mtPF mixture-treated autologous plasma, but did not show statistical significance when compared to PMNs exposed to untreated plasma (FIGS. 12D and 13D). On admission, the plasma LTB4 levels of patients with septic shock and patients negative for secondary infection were 88 pg/mL and 84 pg/mL, respectively (Tables 2 and 4). However, at the start of the secondary infection, the LTB4 level of the septic shock patient who developed secondary infection was 91 pg/mL, which was significantly lower than the LTB4 level of the secondary infection-negative patient (FIG. 13C) (Table 4). This is consistent with the previous study results of the inventors of the present disclosure showing that the plasma LTB4 levels of patients recovering from septic shock who developed secondary infection were lower than those of patients negative for secondary infection. Another experimental study reported that LTB4 acts as a signal relay molecule during PMN chemotaxis and LTB4 enhances PMN polarization and amplifies PMN migration in response to fMLF.

Therefore, we also investigated the effect of additional treatment with LTB4 on the chemotaxis of PMNs exposed to bead-anti-mtFP mixture-treated plasma in septic shock patients who developed secondary infections. 50 pg/mL of recombinant LTB4 was added to the bead-anti-mtFP mixture treated plasma at the start of incubation with PMNs obtained from the same patient. After 90 minutes of incubation, PMN chemotaxis was measured. A 90-minute exposure to bead-anti-mtFP mixture treated plasma with additional recombinant LTB4 effectively restored PMN chemotaxis compared to PMN exposed to untreated plasma (FIG. 13D). The above results suggest that plasma LTB4 may play a key role in the restoration of FPR-mediated PMN chemotaxis after the removal of circulating mtFP, and plasma LTB4 levels may be a possible biomarker to predict the development of immune paralysis in patients recovering from septic shock.

In other words, the removal of circulating potent mtFP rescued FPR1-mediated PMN chemotaxis in patients recovering from septic shock who developed secondary infection. In particular, the bead-anti-mtFP mixture prepared by binding the protein A/sepharose to anti-mtFP antibodies specific for ND6, ND3, ND4 and ND5 successfully removed circulating potent mtFP and restored PMN chemotaxis. In clinical settings, the removal of circulating mtFP through blood perfusion using extracorporeal membranes attaching anti-mtFP antibodies could be considered as an adjuvant therapeutic strategy to inhibit PMN chemotactic anergy. Inhibiting the development of secondary nosocomial infections in patients who survive the hyperinflammatory phase may improve the long-term clinical outcome of patients with septic shock.

What is claimed is:

1. A blood perfusion device, comprising:

a blood inlet configured to allow blood to flow into the device;

an adsorption medium comprising an anti-mitochondrial N-formyl peptides antibody (anti-mtFP antibody); and a blood outlet configured to allow blood to flow out of the device, wherein the anti-mtFP antibody is an antibody to at least one of mitochondrial NADH-ubiquinone oxidoreductase chain 6 (MT-ND6), MT-ND3, MT-ND4, MT-ND5, or mitochondrial cytochrome c oxidase 1 (MT-COX1).

2. The blood perfusion device of claim 1, wherein the blood perfusion device suppresses the occurrence of secondary infection in hospital.

3. The blood perfusion device of claim 1, wherein the blood perfusion device further comprises oxygen, a blood-anticoagulant, and leukotriene B4 (LTB4).

4. The blood perfusion device of claim 1, wherein the adsorption medium comprises the anti-mtFP antibody at a concentration of 0.5 μg/mL to 20.0 μg/mL.

5. The blood perfusion device of claim 1, wherein the adsorption medium has the anti-mtFP antibody attached or coated on a surface thereof.

6. The blood perfusion device of claim 1, wherein the adsorption medium is at least one selected from the group consisting of fiber form, bead form, film form, and hollow-fiber form.

7. A method for reducing secondary infection in hospital, comprising:

(a) passing blood obtained from a subject through a device comprising an adsorption medium comprising an anti-mitochondrial N-formyl peptides antibody (anti-mtFP antibody);

(b) producing blood with a reduced level of mitochondrial N-formyl peptides (mtFP) in the blood; and (c) injecting the blood with a reduced mtFP level into the subject.

8. The method of claim 7, wherein the subject is one selected from sepsis patients, septic shock patients, severe trauma patients, organ transplant patients, hemorrhagic shock patients, myocardial infarction patients, cardiogenic shock patients, stroke patients, or patients surviving after cardiac arrest.

* * * * *